United States Patent
Szillat et al.

(10) Patent No.: US 9,260,454 B2
(45) Date of Patent: Feb. 16, 2016

(54) ISOTHIAZOLOPYRIDINE-2-CARBOXAMIDES AND THEIR USE AS PHARMACEUTICALS

(71) Applicant: Sanofi, Paris (FR)

(72) Inventors: Hauke Szillat, Frankfurt (DE); Thomas Leeuw, Eltville (DE); Martin Lorenz, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/307,961

(22) Filed: Jun. 18, 2014

(65) Prior Publication Data

US 2014/0296169 A1     Oct. 2, 2014

Related U.S. Application Data

(63) Continuation of application No. PCT/EP2012/075932, filed on Dec. 18, 2012.

(30) Foreign Application Priority Data

Dec. 20, 2011   (EP) ...................................... 11306711

(51) Int. Cl.
*C07D 513/04*    (2006.01)
*C07D 519/00*    (2006.01)

(52) U.S. Cl.
CPC ............ *C07D 513/04* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 3,892,745 | A | 7/1975 | Tomita et al. |
| 3,965,107 | A | 6/1976 | Rainey et al. |
| 4,512,985 | A | 4/1985 | Maignan et al. |
| 8,148,395 | B2 | 4/2012 | Zoller et al. |
| 2002/0132776 | A1 | 9/2002 | Fuchsbauer et al. |
| 2011/0229568 | A1 | 9/2011 | Oertel |

FOREIGN PATENT DOCUMENTS

| | | |
|---|---|---|
| CN | 101415706 | 4/2009 |
| EP | 0411701 | 2/1991 |
| WO | 2004/094393 | 11/2004 |
| WO | 2004/094394 | 11/2004 |
| WO | WO 2004/113363 | 12/2004 |
| WO | 2005/089753 | 9/2005 |
| WO | 2007/110216 | 10/2007 |
| WO | WO 2011/060321 | 5/2011 |
| WO | WO2011/157827 | * 12/2011 |
| WO | WO 2011/157827 | 12/2011 |

OTHER PUBLICATIONS

International Search Report for WO2013/092574 dated. Jun. 27, 2013.

Siegel, et al., Transglutaminase 2 Inhibitors andTheir Therapeutic Role in Disease States, Pharmacology & Therapeutics, vol. 115, (2007), pp. 232-245.
Wright, et al., Heteroaryl-Fused 2-Phenylisothiazolone Inhibitors of Cartilage Breakdown, J. Med. Chem., (1994), vol. 37, pp. 3071-3078.
Lorand, et al., Transglutaminases: Crosslinking Enzymes With Pleiotropic Functions, Nat. Rev. Mol. Cell Biol. (2003), vol. 4, pp. 140-156.
Iismaa, et al., Transglutaminases and Disease: Lessons From Genetically Engineered Mouse Models and Inherited Disorders, Physiol. Rev., vol. 89, pp. 991-1023, (2009).
Wang, et al., TG2, A Novel Extracellular Protein With Multiple Functions, Amino Acids, (2012), vol. 42, pp. 939-949.
Rosenthal, et al., Transglutaminase Activity in Aging Articular Cartilage Vesicles, Arthritis & Rheumatism, vol. 40, No. 5, (1997), pp. 965-970
Johnson, et al., Interleukin-1 Induces Pro-Mineralizing Activity of Cartilage Tissue Transglutaminase and Factor XIIIa, American Journal of Pathology, vol. 159, No. 1, (2001), pp. 149-163.
Nurminsky, et al., Transglutaminase 2 Regulates Early Chondrogenesis and Glycosaminoglycsan and Synthesis, Mechanisms of Development, vol. 128, (2011), pp. 234-245.
Nurminskaya, et al., Plasma Transglutaminase in Hypertrophic Chondrocytes: Expression and Cell-Specific Intracellular Activation Produce Cell Death and Externalization, The Journal of Cell Biology, vol. 142, No. 4, pp. 1135-1144, (1998).
Thomazy, et al., Expression of Tissue Transglutaminase in the Developing Chicken Limb is Associated Both With Apoptosis and Endochondral Ossification, Cell Death and Differentiation, (1999), vol. 6, pp. 145-154.
Orlandi, et al., Transglutaminase-2 Differently Regulates Cartilage Destruction and Osteophyte Formation in a Surgical Model of Osteoarthritis, Amino Acids; (2009), vol. 36, pp. 755-765.

(Continued)

*Primary Examiner* — Timothy R Rozof
(74) *Attorney, Agent, or Firm* — Kelly L. Bender

(57) ABSTRACT

The present disclosure relates to substituted isothiazolo[5,4-b]pyridine-2-carboxamides of the formula I,

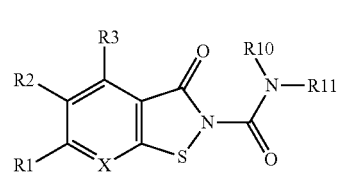

in which R1, R2, R3, R10, R11 and X are as defined in the claims. The compounds of the formula I are inhibitors of transglutaminases, in particular transglutaminase 2 (TGM2), and are suitable for the treatment of various diseases, for example degenerative joint diseases such as osteoarthritis. The invention furthermore relates to processes for the preparation of the compounds of the formula I, their use as pharmaceuticals, and pharmaceutical compositions comprising them.

20 Claims, No Drawings

(56) References Cited

OTHER PUBLICATIONS

Rosenthal, et al., Participation of Transglutaminase in the Activation of Latent Transforming Growth Factor β1 in Aging Articular Cartilage, Arthritis & Rheumatism, vol. 43, No. 8, (2000), pp. 1729-1733.

Andreae, N-Unsubstituted Sulfenamides by Electrophilic Amination of Mercapto Compounds, J. Prakt. Chem. vol. 339, (1997); pp. 152-158.

Chiyoda, et al., Convenient Synthesis of 1,2-Benzisothiazol-3(2H)-Ones by Cyclization Reaction of Acyl Azide, Synlett, (2000), vol. 10, pp. 1427-1428.

Furdas, et al., Synthesis and Biological Testing of Novel Pyridoisothiazolones as Histone Acetyltransferase Inhibitors, Bioorganic & Medicinal Chemistry, vol. 19, (2011), pp. 3678-3689.

Oertel, et al., A Highly Sensitive Fluorometric Assay for Determination of Human Coagulation Factor XIII in Plasma, Analytical Biochemistry, vol. 367, (2007), pp. 152-158

Wright, et al., An Efficient Preparation of 2H-[5,4-b]-Pyridoisothiazolone, Org. Prep. Proced. Int., (1993), vol. 25, pp. 247-249.

Zawisza, et al., Synthesis and Properties of Some Derivatives of 2H-4,6-Dimethylpyrido[3,2-d] Isothiazolin-3-one, Il Farmaco Ed. Sci., (1985), vol. 40, pp. 124-132.

* cited by examiner

ISOTHIAZOLOPYRIDINE-2-CARBOXAMIDES AND THEIR USE AS PHARMACEUTICALS

This application is a continuation of International Application No. PCT/EP2012/075932, filed Dec. 18, 2012, which is incorporated herein by reference in its entirety; which claims priority to European Patent Application No. 11306711.0, filed Dec. 20, 2011.

The present invention relates to substituted isothiazolo[5,4-b]pyridine-2-carboxamides of the formula I,

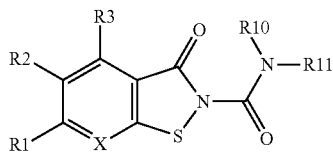

in which R1, R2, R3, R10, R11 and X are as defined below. The compounds of the formula I are inhibitors of transglutaminases, in particular transglutaminase 2 (TGM2), and are suitable for the treatment of various diseases, for example degenerative joint diseases such as osteoarthritis. The invention furthermore relates to processes for the preparation of the compounds of the formula I, their use as pharmaceuticals, and pharmaceutical compositions comprising them.

Transglutaminase 2 (TGM2) belongs to a family of nine transglutaminases, including the active enzymes transglutaminases 1 to 7 and factor XIIIA (FXIIIa), as well as the enzymatically inactive erythrocyte protein band 4.2 (EPB42) (Lorand, L. et al., Transglutaminases: crosslinking enzymes with pleiotropic functions, Nat. Rev. Mol. Cell Biol. 2003, 4: 140-156; Iismaa, S. E. et al., Transglutaminases and disease: lessons from genetically engineered mouse models and inherited disorders, Physiol. Rev. 2009; 89: 991-1023; Wang, Z. et al., TG2, a novel extracellular protein with multiple functions, Amino Acids, 2012, 42: 939-949, published online on Aug. 5, 2011). Other names of TGM2 are TG2, tissue transglutaminase, tTG, TGC and Gha. TGM2 is the HUGO (Human Genome Organization) name.

Transglutaminases are enzymes that catalyze the crosslinking of intermolecular bonds between glutamine and lysine side-chains in peptides, resulting in the formation of ε-(γ-glutamyl)lysine isopeptide bonds ((Lorand et al.). The overall primary structure of transglutaminases is not highly conserved. However, they have a high degree of sequence similarity within the transglutaminase domain active center, and based on the structure of the active center they all belong to the superfamily of papain-like cysteine proteases. All enzymes belonging to this family possess the catalytic triad Cys-His-Asp or Cys-His-Asn. The activity of transglutaminases is calcium-dependent. In addition to protein crosslinking, transglutaminases can modify proteins by amine incorporation and deamidation, and by acting as an isopeptidase in a $Ca^{2+}$-dependent manner. Transglutaminases have high specificity for the glutamine substrate, but weaker specificity toward the acyl-acceptor amino group which can be either an ε-amino group of the peptide lysine, or a low molecular primary amine or polyamine.

In addition to its transglutaminase activity, TGM2 acts as a multi-functional enzyme. With its GTP binding domain TGM2 binds guanosine triphosphate (GTP) and guanosine diphosphate (GDP). TGM2 has GTPase activity. Binding of GTP inhibits the interaction with $Ca^{2+}$ and decreases the transglutaminase activity, whereas an increasing $Ca^{2+}$ concentration inhibits binding of GTP (Lorand et al.; Iismaa et al.).

Although it does not contain a typical consensus kinase domain, TGM2 also has intrinsic serine/threonine kinase activity with, for example, insulin-like growth factor binding protein (IGFBP), p53 tumor suppressor protein, or histones as substrates. TGM2 kinase activity is reduced by high $Ca^{2+}$ concentrations and increased by ATP. Furthermore, TGM2 has extracellular protein disulfide isomerase (PDI) activity that does not require the presence of $Ca^{2+}$ and is independent of transglutaminase or GTPase activities (Iismaa et al.).

TGM2 is expressed in most tissues and cell types with constitutive expression, for example, in endothelial cells, smooth muscle cells, chondrocytes, fibroblasts, neuronal cells, and many others (Lorand et al.; Iismaa et al.). The expression of TGM2 is frequently upregulated by a number of physiological and pathological stimuli and, for example, retinoic acid or a number of inflammatory cytokines and growth factors including TGFβ (transforming growth factor β), TNFα (tumor necrosis factor α), and IL6 (interleukin 6) can induce TGM2 expression (Wang et al.). Pathologically upregulated expression of TGM2 is associated with a number of diseases that include metastatic cancer, celiac disease, tissue fibrosis, neurodegenerative diseases, and osteoarthritis (Iismaa et al.).

While TGM2 is able to fulfill several different functions, the regulation of its activity is closely related to its cellular and sub-cellular localization under different physiological and pathological conditions. It is found in cytosol, nucleus, mitochondria, but also extra-cellular, whereby the mechanism for secretion of TGM2 has not been elucidated so far (Lorand et al.; Iismaa et al.; Wang et al.). Unlike classic secretory proteins, TGM2 does not possess a hydrophobic leader sequence and thus cannot be secreted via conventional ER (endoplasmatic reticulum)/Golgi-dependent pathways. FXIIIa as example for another transglutaminase is secreted as a pro-enzyme and activated extracellularly by proteolysis through thrombin cleavage. TGM2 can interact with a large number of cell surface proteins, is involved in cellular signaling regulation, and acts as regulator of intracellular signaling downstream of several cell surface receptors (Lorand et al.; Iismaa et al.). It can act as G protein Gh in response to agonist activation of the thromboxane receptor TPα and signal through phospholipase C. TGM2 has also been demonstrated to facilitate cell adhesion by interacting directly, for example, with several integrins, with syndecan 4, or with the orphan G protein-coupled cell adhesion receptor GPR56 (Iismaa et al.).

TGM2 and, at a much lower basal concentration, FXIIIa, are the only transglutaminases expressed in cartilage and osseous tissues. The expression of both increases strongly with increase in age and in osteoarthritic cartilage, for example in superficial and deep zones of knee osteoarthritis (OA) articular cartilage as well as the chondrocyte zone of OA menisci (Rosenthal, A. K. et al., Transglutaminase activity in aging articular chondrocytes and articular cartilage vesicles, Arthritis Rheum. 1997, 40: 966-970; Johnson, K. et al., Interleukin-1 induces pro-mineralizing activity of cartilage tissue transglutaminase and factor XIIIa, Am. J. Pathol. 2001, 159: 149-163). In accordance with this, the expression of TGM2 is increased in vitro and in vivo in hypertrophic chondrocytes of different species including human, and a clear association for an increase in cartilage protein-transglutamination and crosslinking with the development of OA has been demonstrated in several species including human (Johnson et al.; Iismaa et al.).

The condensation of mesenchymal stem cells induces their differentiation into chondrocytes. This differentiation process passes through several sequential steps of maturation phases, including a proliferation phase, a pre-hypertrophic phase, and finally the terminal maturation that is characterized by chondrocyte hypertrophy and extracellular matrix (ECM) calcification and mineralization. Matrix synthesis, which is required for maintaining the healthy and functional cartilage, is highest in proliferating chondrocytes and slowly declines with advanced maturation. Thus, understanding principles that contribute to the functional decline in cartilage function is required to develop therapeutic approaches for cartilage diseases such as osteoarthritis or degenerative disk disease. TGM2 and FXIIIa transglutaminase activity promotes cell differentiation towards a pre-hypertrophic stage with increased expression of, for example, Ihh (Indian hedgehog), FXIIIa, and Runx2 (Runt-related transcription factor 2) as typical markers of chondrocyte hypertrophy (Nurminsky, D. et al., Transglutaminase 2 regulates early chondrogenesis and glycosaminoglycan synthesis, Mechanisms Developm. 2011, 128: 234-245). In accordance with this, both transglutaminases have similar substrate specificity and enhance terminal maturation in differentiating osteochondral cells in vitro (Nurminsky et al.; Nurminskaya, M. et al., Plasma transglutaminase in hypertrophic chondrocytes: expression and cell-specific intracellular activation produce cell death and externalization, J. Cell Biol. 1998, 142: 1135-1144). Underlining its role in pre-/hypertrophic chondrocytes, TGM2 expression is not detectable at early stages of chondrocyte differentiation in vivo in the developing "cartilaginous analog" of endochondral bones. However, its expression increases during hypertrophic differentiation, and the maturation of the cartilage is characterized by intracellular and extracellular transglutaminase accumulation in the zone of hypertrophic chondrocytes (Nurminsky et al.; Thomázy, V. A. et al., Expression of tissue transglutaminase in the developing chicken limb is associated both with apoptosis and endochondral ossification, Cell Death Differ. 1999, 6: 146-154). Chondrocyte hypertrophy, together with increased transglutaminase activity, promotes successive pathological calcification, colocalized with deposits of calcium pyrophosphate dihydrate (CPPD) crystals.

The in vivo situation for chondrogenic differentiation is mimicked in vitro in high-density cell cultures of mesenchymal cells, described also as micromass cultures. In such a system, the forced overexpression of TGM2 promotes the transition of chondrocytes into the pre-hypertrophic stage, and it inhibits the production of the proteoglycan cartilage matrix and the enlargement of chondrogenic nodules. The enhanced TGM2 expression decreases expression and activity of xylosyltransferase-2 (Xylt2) as one of the key enzymes of protein glycosylation, thereby attenuating deposition of the cartilaginous extracellular matrix. In contrast to this, pharmacological inhibition of both, TGM2 and FXIIIa transglutaminase activity in micromass culture with 30 μM of the non-specific ERW1069 transglutaminase inhibitor leads to an increase in Xylt2 expression and proteoglycan deposition (Nurminsky et al.).

In knock-out mouse models for TGM2 the absence of TGM2 protein in the homozygote progeny was clearly demonstrated. The homozygous deletion of TGM2, however, does not result in an embryonic lethal phenotype, and the TGM2−/− mice do not show any obvious abnormal phenotype. They are viable, of normal size and weight, and born with mendelian frequency (Iismaa et al.; Orlandi et al., Transglutaminase-2 differently regulates cartilage destruction and osteophyte formation in a surgical model of osteoarthritis, Amino Acids 2009, 36: 755-763). Also, no skeletal phenotype has been observed in either TGM2 or FXIIIa knock-out models under normal conditions, which may be explained by the ability of the two enzymes to compensate for each other.

However, chondrocytes prepared from TGM2−/− mice are protected from IL-1β (interleukin 1β) and ATRA (all-trans retinoic acid) induced hypertrophic differentiation. Furthermore, TGM2−/− mice were used to follow the progression of cartilage destruction and bone remodeling surgically-induced knee joint instability in comparison to wild-type mice. As described in Orlandi et al., in experiments performed in order to induce joint instability, the anterior and posterior cruciate ligaments as well as the medial and lateral collateral ligaments were transected, and the medial and lateral menisci were removed. Changes in cartilage were investigated by histomorphometrical, radiological and immuno-histochemical methods during a time course of up to eight weeks. This set of experiments showed that the degree of cartilage destruction is less in TGM2−/− mice than in wild-type mice.

However, in the TGM2−/− mice compensatory mechanisms result in the increased expression of FXIIIA and TGFβ1 in bone and cartilage. Elevated TGFβ1 activity has been shown to be associated with elevated bone mass and osteoarthritis, and the injection of TGFβ1 induces osteoarthritis-like changes and osteophyte formation in the murine knee joint. Furthermore, TGM2 and FXIIIa participate in the activation of the latent TGFβ complex (LTGFβ). In accordance with this, an increase in the number of osteophytes is observed in TGM2−/− mice with surgically induced joint instability (Orlandi et al.). Unspecific transglutaminase inhibitors such as, for example, cystamine, however, decrease active TGFβ1 in chondrocytes (Orlandi et al.; Rosenthal, A. K. et al., Participation of transglutaminase in the activation of latent transforming growth factor beta1 in aging articular cartilage, Arthritis Rheum. 2000, 43: 1729-1733).

Taken together, the inhibition of transglutaminase activity in osteoarthritic cartilage is leading to a reduction in pathological matrix calcification, and to an increase in matrix deposition supporting cartilage regeneration in disorders such as degenerative joint diseases and degenerative intervertebral disk diseases. Thus, there is a need for compounds which inhibit transglutaminase activity, in particular TGM2 activity, and can be used for the treatment of such diseases or other diseases in which a reduced transglutaminase activity is desired.

Certain compounds capable of inhibiting transglutaminases have already been described, for example in EP 0411701, US 2002/0132776, US 2011/0229568, WO 2004/113363 or WO 2011/060321. However, in part they suffer from the drawbacks associated with their peptidic structures, and their property profile still is not satisfactory, for example for the treatment of degenerative joint diseases and intervertebral disk diseases, such as osteoarthritis, for example. Thus, there is a need for further compounds which inhibit transglutaminases and have a suitable property profile, for example with respect to their inhibitory specificity, and are suitable for use as pharmaceuticals in the treatment of the mentioned disease states. It has now been found that the isothiazolopyridine-2-carboxamides of the formula I inhibit transglutaminases, in particular TGM2, and have a suitable property profile for the desired use.

Certain isothiazolopyridine-2-carboxamides in which the group X in formula I is =N— and the group R10 is hydrogen, which compounds are not comprised by the present invention, have been described, for example compounds in which the groups R1, R2 and R3 in formula I are hydrogen and the group R11 is an alkyl group, a cyclohexyl group or a phenyl group in U.S. Pat. No. 4,512,985 and in Andreae, S., J. prakt. Chem. 1997, 339: 152-158, and compounds in which the groups R1 and R3 in formula I are methyl, the group R2 is hydrogen and the group R11 is a cyclohexyl group or a phenyl group in U.S. Pat. No. 3,965,107 and in Zawisza, T. et al., Farmaco Ed. Sci. 1985, 40: 124-132. The compound of the formula I in which X is =N—, R1, R2 and R3 are hydrogen, and R10 and R11 are ethyl, which may be named as 3-oxo-3H-isothiazolo[5,4-b]pyridine-2-carboxylic acid diethylamide or N,N-diethyl-3-oxo-3H-isothiazolo[5,4-b]pyridine-2-carboxamide or N,N-diethyl-3-oxo-isothiazolo[5,4-b]pyridine-2(3H)-carboxamide, for example, has already been disclosed. A TGM2 inhibitory activity of these compounds has not been described.

Thus, a subject of the present invention are the compounds of the formula I, in any of their stereoisomeric forms and mixtures of stereoisomeric forms in any ratio, and the pharmaceutically acceptable salts thereof,

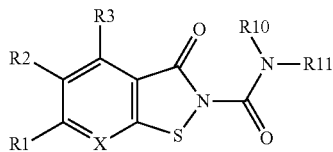

I wherein

X is selected from the series consisting of =N— and =N(O)—;

R1, R2 and R3 are independently of one another selected from the series consisting of hydrogen, halogen, $(C_1-C_4)$-alkyl, $(C_1-C_4)$-alkyl-O—, nitro, cyano, $(C_1-C_4)$-alkyl-O—C(O)—, R4-N(R5)-C(O)— and R6-N(R7)-S(O)$_2$—;

R4 is selected from the series consisting of hydrogen, $(C_1-C_4)$-alkyl, $(C_3-C_7)$-cycloalkyl, $(C_3-C_7)$-cycloalkyl-$(C_1-C_4)$-alkyl-, phenyl, phenyl-$(C_1-C_4)$-alkyl-, Het1 and Het1-$(C_1-C_4)$-alkyl-, wherein Het1 is optionally substituted by one or more identical or different substituents R8;

R5, R6 and R7 are independently of one another selected from the series consisting of hydrogen, $(C_1-C_4)$-alkyl, $(C_3-C_7)$-cycloalkyl and $(C_3-C_7)$-cycloalkyl-$(C_1-C_4)$-alkyl-;

R8 is selected from the series consisting of halogen, $(C_1-C_4)$-alkyl, hydroxy, oxo, $(C_1-C_4)$-alkyl-O— and cyano;

R10 is selected from the series consisting of hydrogen, $(C_1-C_4)$-alkyl, $(C_3-C_7)$-cycloalkyl, $(C_3-C_7)$-cycloalkyl-$(C_1-C_4)$-alkyl- and $(C_1-C_4)$-alkyl-O—$(C_1-C_4)$-alkyl-, with the proviso that R10 can only be hydrogen if X is =N(O)—;

R11 is selected from the series consisting of $(C_1-C_4)$-alkyl which is optionally substituted by one or more identical or different substituents R12, $(C_3-C_7)$-cycloalkyl which is optionally substituted by one or more identical or different substituents R13, and Het2 which is optionally substituted by one or more identical or different substituents R14 and wherein Het2 is bonded via a ring carbon atom;

or the groups R10 and R11, together with the nitrogen atom carrying them, form a 4-membered to 12-membered, monocyclic or bicyclic, saturated or partially unsaturated heterocycle which, in addition to the nitrogen atom carrying R10 and R11, comprises 0, 1 or 2 further ring heteroatoms selected from the series consisting of nitrogen, oxygen and sulfur, which is optionally substituted on ring carbon atoms by one or more identical or different substituents R30, and which is optionally substituted on further ring nitrogen atoms by one or more identical or different substituents R40;

R12 is selected from the series consisting of $(C_3-C_7)$-cycloalkyl, phenyl, Het3, hydroxy, $(C_1-C_4)$-alkyl-O—, $(C_1-C_4)$-alkyl-C(O)—O—, R15-N(R16)- and R17-C(O)—N(R18)-, wherein phenyl and Het3 independently of one another are optionally substituted by one or more identical or different substituents R19;

R13 is selected from the series consisting of hydroxy, $(C_1-C_4)$-alkyl-O—, $(C_1-C_4)$-alkyl-C(O)—O— and cyano;

R14 is selected from the series consisting of fluorine, $(C_1-C_4)$-alkyl, hydroxy, $(C_1-C_4)$-alkyl-O—, $(C_1-C_4)$-alkyl-C(O)—O—, HO—$(C_1-C_4)$-alkyl-, $(C_1-C_4)$-alkyl-O—$(C_1-C_4)$-alkyl-, $(C_1-C_4)$-alkyl-C(O)—O—$(C_1-C_4)$-alkyl- and $(C_1-C_4)$-alkyl-C(O)—;

R15, R16 and R18 are independently of one another selected from the series consisting of hydrogen, $(C_1-C_4)$-alkyl, $(C_3-C_7)$-cycloalkyl and $(C_3-C_7)$-cycloalkyl-$(C_1-C_4)$-alkyl-;

R17 is selected from the series consisting of $(C_1-C_4)$-alkyl, $(C_3-C_7)$-cycloalkyl, $(C_3-C_7)$-cycloalkyl-$(C_1-C_4)$-alkyl-, phenyl and phenyl-$(C_1-C_4)$-alkyl-;

R19 is selected from the series consisting of halogen, $(C_1-C_4)$-alkyl, hydroxy, $(C_1-C_4)$-alkyl-O—, $(C_1-C_4)$-alkyl-C(O)—O—, cyano, R20-O—C(O)— and R21-N(R22)-C(O)—;

R20, R21 and R22 are independently of one another selected from the series consisting of hydrogen and $(C_1-C_4)$-alkyl;

R30 is selected from the series consisting of fluorine, $(C_1-C_4)$-alkyl, Het2, hydroxy, oxo, $(C_1-C_4)$-alkyl-O—, R31-N(R32)-, $(C_1-C_4)$-alkyl-C(O)—, R33-O—C(O)— and R34-N(R35)-C(O)—, wherein Het2 is optionally substituted by one or more identical or different substituents R36;

R31, R32, R33, R34 and R35 are independently of one another selected from the series consisting of hydrogen and $(C_1-C_4)$-alkyl;

R36 is selected from the series consisting of fluorine, $(C_1-C_4)$-alkyl, hydroxy and oxo;

R40 is selected from the series consisting of $(C_1-C_4)$-alkyl which is optionally substituted by one or more identical or different substituents R41, $(C_3-C_7)$-cycloalkyl which is optionally substituted by one or more identical or different substituents R42, phenyl which is optionally substituted by one or more identical or different substituents R43, Het1 which is optionally substituted by one or more identical or different substituents R44, $(C_1-C_4)$-alkyl-C(O)— which is optionally substituted by one or more identical or different substituents R45, $(C_3-C_7)$-cycloalkyl-C(O)— which is optionally substituted by one or more identical or different substituents R46, phenyl-C(O)— which is optionally substituted by one or more identical or different substituents R47, Het3-C(O)— which is optionally substituted by one or more identical or different substituents R48 and wherein Het3 is bonded via a ring carbon atom, R49-N(R50)-C(O)—, $(C_1-C_4)$-alkyl-S(O)$_2$— and R51-N(R52)-S(O)$_2$—;

R41 is selected from the series consisting of $(C_3-C_7)$-cycloalkyl, hydroxy, $(C_1-C_4)$-alkyl-O—, R60-N(R61)-, R62-O—C(O)— and R63-N(R64)-C(O)—;

R42 is selected from the series consisting of hydroxy and R65-N(R66)-;

R43 is selected from the series consisting of halogen, $(C_1-C_4)$-alkyl, hydroxy, $(C_1-C_4)$-alkyl-O—, cyano, R67-O—C(O)— and R68-N(R69)-C(O)—;

R44 is selected from the series consisting of halogen, $(C_1-C_4)$-alkyl, hydroxy, oxo, $(C_1-C_4)$-alkyl-O—, R70-N(R71)-, $(C_1-C_4)$-alkyl-C(O)—N(R72)-, $(C_1-C_4)$-alkyl-S(O)$_2$—N(R73)- and Het4, wherein Het4 is optionally substituted by one or more identical or different substituents R74;

R45 is selected from the series consisting of $(C_3-C_7)$-cycloalkyl, cyano, hydroxy, $(C_1-C_4)$-alkyl-O—, phenyl-O—, phenyl-$(C_1-C_4)$-alkyl-O—, oxo, R75-N(R76)- and R77-C(O)—N(R78)-;

R46 is selected from the series consisting of hydroxy and R79-N(R80)-;

R47 is selected from the series consisting of halogen, $(C_1-C_4)$-alkyl, $(C_1-C_4)$-alkyl-O— and R81-N(R82)-C(O)—;

R48 is selected from the series consisting of halogen, $(C_1-C_4)$-alkyl, hydroxy, oxo and $(C_1-C_4)$-alkyl-O—;

R49 and R51 are independently of one another selected from the series consisting of hydrogen, $(C_1-C_4)$-alkyl, $(C_3-C_7)$-cycloalkyl, $(C_3-C_7)$-cycloalkyl-$(C_1-C_4)$-alkyl-, phenyl and phenyl-$(C_1-C_4)$-alkyl-;

R50 and R52 are independently of one another selected from the series consisting of hydrogen, $(C_1-C_4)$-alkyl, $(C_3-C_7)$-cycloalkyl and $(C_3-C_7)$-cycloalkyl-$(C_1-C_4)$-alkyl-;

R60, R61, R62, R63, R64, R65, R66, R67, R68, R69, R70, R71, R72, R73, R76, R78, R79, R80, R81, R82, R83 and R84 are independently of one another selected from the series consisting of hydrogen and $(C_1-C_4)$-alkyl;

R74 is selected from the series consisting of fluorine and $(C_1-C_4)$-alkyl;

R75 is selected from the series consisting of hydrogen, $(C_1-C_4)$-alkyl, $(C_3-C_7)$-cycloalkyl, $(C_3-C_7)$-cycloalkyl-$(C_1-C_4)$-alkyl-, phenyl and phenyl-$(C_1-C_4)$-alkyl-;

R77 is selected from the series consisting of $(C_1-C_4)$-alkyl and R83-N(R84)-$(C_1-C_4)$-alkyl-;

Het1 is a monocyclic, 4-membered to 7-membered, saturated, partially unsaturated or aromatic heterocycle which comprises 1, 2 or 3 identical or different ring heteroatoms selected from the series consisting of nitrogen oxygen and sulfur, and which is bonded via a ring carbon atom;

Het2 is a monocyclic, 4-membered to 7-membered, saturated heterocycle which comprises 1 or 2 identical or different ring heteroatoms selected from the series consisting of nitrogen, oxygen and sulfur;

Het3 is a monocyclic or bicyclic, 4-membered to 12-membered, saturated, partially unsaturated or aromatic heterocycle which comprises 1, 2 or 3 identical or different ring heteroatoms selected from the series consisting of nitrogen, oxygen and sulfur;

Het4 is a monocyclic, 4-membered to 7-membered, saturated heterocycle which comprises a ring nitrogen atom via which Het4 is bonded, and 0 or 1 further ring heteroatom selected from the series consisting of nitrogen, oxygen and sulfur;

wherein all phenyl groups are optionally substituted by one or more identical or different substituents selected from the series consisting of halogen, $(C_1-C_4)$-alkyl, cyano, hydroxy and $(C_1-C_4)$-alkyl-O—, unless specified otherwise;

wherein all cycloalkyl groups, independently of any other substituents which can be present on a cycloalkyl group, are optionally substituted by one or more identical or different substituents selected from the series consisting of fluorine and $(C_1-C_4)$-alkyl;

wherein all alkyl groups, independently of any other substituents which can be present on an alkyl group, are optionally substituted by one or more fluorine substituents;

with the proviso that the compound of the formula I is not 3-oxo-3H-isothiazolo[5,4-b]pyridine-2-carboxylic acid diethylamide.

If structural elements such as groups or substituents, for example, can occur several times in the compounds of the formula I, they are all independent of each other and can in each case have any of the indicated meanings, and they can in each case be identical to or different from any other such element. In a dialkylamino group, for example, the alkyl groups can be identical or different.

Alkyl groups, i.e. saturated hydrocarbon residues, can be linear (straight-chain) or branched. This also applies if these groups are substituted or are part of another group, for example an alkyl-O— group (alkyloxy group, alkoxy group) or an HO-substituted alkyl group (HO-alkyl-, hydroxyalkyl group). Depending on the respective definition, the number of carbon atoms in an alkyl group can be 1, 2, 3 or 4, or 1, 2 or 3, or 1 or 2, or 1. Examples of alkyl are methyl, ethyl, propyl including n-propyl and isopropyl, butyl including n-butyl, sec-butyl, isobutyl and tert-butyl. Examples of alkyl-O— groups are methoxy, ethoxy, n-propoxy, isopropoxy, n-butoxy, isobutoxy, tert-butoxy. Examples of alkyl-$S(O)_2$— are methanesulfonyl ($CH_3$—$S(O)_2$—), ethanesulfonyl ($CH_3$—$CH_2$—$S(O)_2$—), 1-methylethanesulfonyl $((CH_3)_2CH$—$S(O)_2$—). In one embodiment of the invention, a $(C_1-C_4)$-alkyl group in any occurrence in the compound of the formula I is independently of any other occurrences a $(C_1-C_3)$-alkyl group, in another embodiment a $(C_1-C_2)$-alkyl group, in another embodiment a methyl group.

A substituted alkyl group can be substituted in any positions, provided that the respective compound is sufficiently stable and is suitable as a pharmaceutical active compound. The prerequisite that a specific group and a compound of the formula I are sufficiently stable and suitable as a pharmaceutical active compound, applies in general with respect to the definitions of all groups in the compounds of the formula I. The term "optionally substituted by", when used with respect to an alkyl group or any other group, which is equivalent to an expression like "can be substituted by", indicates that the respective group is unsubstituted, i.e. does not carry any of the specified substituents, or is substituted by the specified substituents. An alkyl group which generally, and independently of any other substituents, is optionally substituted by one or more fluorine substituents, is unsubstituted by fluorine substituents, i.e. does not carry fluorine substituents, or is substituted, for example by 1, 2, 3, 4, 5, 6, 7, 8 or 9 fluorine substituents, or by 1, 2, 3, 4 or 5 fluorine substituents, or by 1, 2 or 3 fluorine substituents, which can be located in any positions. For example, in a fluoro-substituted alkyl group one or more methyl groups can carry three fluorine substituents each and be present as trifluoromethyl groups, and/or one or more methylene groups ($CH_2$) can carry two fluorine substituents each and be present as difluoromethylene groups. The explanations with respect to the substitution of a group by fluorine also apply if the group additionally carries other substituents and/or is part of another group, for example of an alkyl-O— group. Examples of fluoro-substituted alkyl groups are trifluoromethyl, 2-fluoroethyl, 1-fluoroethyl, 1,1-difluoroethyl, 2,2,2-trifluoroethyl, pentafluoroethyl, 3,3,3-trifluoropropyl, 2,2,3,3,3-pentafluoropropyl, 4,4,4-trifluorobutyl and heptafluoroisopropyl. Examples of fluoro-substituted alkyl-O— groups are trifluoromethoxy, 2,2,2-trifluoroethoxy, pentafluoroethoxy and 3,3,3-trifluoropropoxy. With respect to all groups or substituents in the compounds of the formula I which can be an alkyl group which can generally contain one or more fluorine substituents, as an example of groups or substituents containing fluorine-substituted alkyl, which may be included in the definition of the group or substituent, the group $CF_3$ (trifluoromethyl), or respective groups such as $CF_3$—O—, may be mentioned. In one embodiment of the invention, an alkyl group in any occurrence in the compound of the formula I is, independently of any other substituents which may be present on it and independently of any other occurrences of alkyl groups, unsubstituted by fluorine, in another embodiment it is substituted by fluorine.

The above explanations with respect to alkyl groups apply correspondingly to alkyl groups which in the definition of a group in the compounds of the formula I are bonded to two adjacent groups, or linked to two groups, and may be regarded as divalent alkyl groups (alkanediyl groups), like in the case of the alkyl part of a substituted alkyl group. Thus, such groups can also be linear or branched, the bonds to the adjacent groups can be located in any positions and can start from the same carbon atom or from different carbon atoms, and they can be unsubstituted or substituted by fluorine substituents independently of any other substituents. Examples of such divalent alkyl groups are —$CH_2$—, —$CH_2$—$CH_2$—, —$CH_2$—$CH_2$—$CH_2$—, —$CH_2$—$CH_2$—$CH_2$—$CH_2$—, —$CH(CH_3)$—, —$C(CH_3)_2$—, —$CH(CH_3)$—$CH_2$—, —$CH_2$—$CH(CH_3)$—, —$C(CH_3)_2$—$CH_2$—, —$CH_2$—$C(CH_3)_2$—. Examples of fluoro-substituted alkanediyl groups, which can contain 1, 2, 3, 4, 5 or 6 fluorine substituents, for example, are —CHF—, —$CF_2$—, —$CF_2$—$CH_2$—, —$CH_2$—$CF_2$—, —$CF_2$—$CF_2$—, —$CF(CH_3)$—, —$C(CF_3)_2$—, —$C(CH_3)_2$—$CF_2$—, —$CF_2$—$C(CH_3)_2$—.

The number of ring carbon atoms in a $(C_3-C_7)$-cycloalkyl group can be 3, 4, 5, 6 or 7. Examples of cycloalkyl are cyclopropyl, cyclobutyl, cyclopentyl, cyclohexyl and cycloheptyl. In one embodiment of the invention, a $(C_3-C_7)$-cycloalkyl group in any occurrence in the compound of the formula I is independently of any other occurrence a $(C_3-C_6)$-cycloalkyl group, in another embodiment a $(C_3-C_4)$-cycloalkyl group, in another embodiment a $(C_5-C_7)$-cycloalkyl group, in another embodiment a $(C_5-C_6)$-cycloalkyl group. Cycloalkyl groups which generally, and independently of any other substituents, are optionally substituted by one or more $(C_1-C_4)$-alkyl substituents, are unsubstituted by alkyl substituents, i.e. do not carry alkyl substituents, or are substituted, for example by 1, 2, 3 or 4 identical or different $(C_1-C_4)$-alkyl substituents, for example by methyl groups, which substituents can be located in any positions. Examples of such alkyl-substituted cycloalkyl groups are 1-methylcyclopropyl, 2,2-dimethylcyclopropyl, 1-methylcyclopentyl, 2,3-dimethylcyclopentyl, 1-methylcyclohexyl, 4-methylcyclohexyl, 4-isopropylcyclohexyl, 4-tert-butylcyclohexyl, 3,3,5,5-tetramethylcyclohexyl. Cycloalkyl groups which generally, and independently of any other substituents, are optionally substituted by one or more fluorine substituents, are unsubstituted by fluorine substituents, i.e. do not carry fluorine substituents, or are substituted, for example by 1, 2, 3, 4, 5, 6, 7, 8, 9, 10 or 11 fluorine substituents, or by 1, 2, 3, 4, 5 or 6 fluorine substituents, or by 1, 2 or 3 fluorine substituents. The fluorine substituents can be located in any positions of the cycloalkyl group and can also be located in an alkyl substituent. Examples of fluoro-substituted cycloalkyl groups are 1-fluorocyclopropyl, 2,2-difluorocyclopropyl, 3,3-difluorocyclobutyl, 1-fluorocyclohexyl, 4,4-difluorocyclohexyl, 3,3,4,4,5,5-hexafluorocyclohexyl. Cycloalkyl groups can also be substituted simultaneously by fluorine and alkyl. In one embodiment of the invention, a cycloalkyl group in any occurrence in the compound of the formula I is, independently of any other substituents which may be present on it and independently of any other occurrences of cycloalkyl groups, unsubstituted by alkyl/and/or fluorine substituents, in another embodiment it is substituted by alkyl and/or fluorine substituents. Examples of the group $(C_3-C_7)$-cycloalkyl-$(C_1-C_4)$-alkyl- are cyclopropylmethyl-, cyclobutylmethyl-, cyclopentylmethyl-, cyclohexylmethyl-, cycloheptylmethyl-, 1-cyclopropylethyl-, 2-cyclopropylethyl-, 1-cyclobutylethyl-, 2-cyclobutylethyl-, 1-cyclopentylethyl-, 2-cyclopentylethyl-, 1-cyclohexylethyl-, 2-cyclohexylethyl-, 1-cycloheptylethyl-, 2-cycloheptylethyl-. In one embodiment of the invention, a $(C_3-C_7)$-cycloalkyl-$(C_1-C_4)$-alkyl-group in any one or more occurrences of such a group, independently of any other occurrences, is a $(C_3-C_7)$-cycloalkyl-$(C_1-C_2)$-alkyl-group, in another embodiment a $(C_3-C_7)$-cycloalkyl-$CH_2$— group. In the group $(C_3-C_7)$-cycloalkyl-$(C_1-C_4)$-alkyl-, and likewise in all other groups, the terminal hyphen denotes the free bond via which the group is bonded, and thus indicates via which subgroup a group composed of subgroups is bonded.

The substituents in substituted phenyl groups can be located in any positions. In monosubstituted phenyl groups, the substituent can be located in position 2, in position 3 or in position 4. In disubstituted phenyl groups, the substituents can be located in positions 2 and 3, in positions 2 and 4, in positions 2 and 5, in positions 2 and 6, in positions 3 and 4, or in positions 3 and 5. In trisubstituted phenyl groups, the substituents can be located in positions 2, 3 and 4, in positions 2, 3 and 5, in positions 2, 3 and 6, in positions 2, 4 and 5, in positions 2, 4 and 6, or in positions 3, 4 and 5. If a phenyl group carries four substituents, some of which can be fluorine atoms, for example, the substituents can be located in positions 2, 3, 4 and 5, in positions 2, 3, 4 and 6, or in positions 2, 3, 5 and 6. If a polysubstituted phenyl group or any other polysubstituted group carries different substituents, each substituent can be located in any suitable position, and the present invention comprises all positional isomers. The number of substituents in a substituted phenyl group can be 1, 2, 3, 4 or 5. In one embodiment of the invention, the number of substituents in a substituted phenyl group, like the number of substituents in any other substituted group which can carry one or more substituents, is 1, 2, 3 or 4, in another embodiment 1, 2 or 3, in another embodiment 1 or 2, in another embodiment 1, where the number of substituents in any occurrence of such a substituted group is independent of the number of substituents in other occurrences. In one embodiment of the invention, unless the substitution of a phenyl group in any occurrence in the compounds of the formula I is specified otherwise, the substituents on optionally substituted phenyl groups are selected from the series consisting of halogen, $(C_1-C_4)$-alkyl and $(C_1-C_4)$-alkyl-O—, in another embodiment from the series consisting of halogen, $(C_1-C_4)$-alkyl and cyano, in another embodiment from the series consisting of halogen and $(C_1-C_4)$-alkyl.

In heterocyclic groups, including the groups Het1, Het2, Het3 and Het4 and heterocycles formed by two groups together with the atom or atoms carrying them, such as the heterocycle which can be formed by R10 and R11 together with the nitrogen atom carrying them, the hetero ring members can be present in any combination and located in any suitable ring positions, provided that the resulting group and the compound of the formula I are suitable and sufficiently stable as a pharmaceutical active compound. In one embodiment of the invention, two oxygen atoms in any heterocyclic ring in the compounds of the formula I cannot be present in adjacent ring positions. In another embodiment of the invention, two hetero ring members selected from the series consisting of oxygen atoms and sulfur atoms cannot be present in adjacent ring positions in any heterocyclic ring in the compounds of the formula I. In another embodiment of the invention, two hetero ring members selected from the series consisting of nitrogen atoms carrying an exocyclic group like a hydrogen atom or a substituent, sulfur atoms and oxygen atoms cannot be present in adjacent ring positions in any heterocyclic ring in the compounds of the formula I. In an aromatic heterocyclic ring the choice of hetero ring members is limited by the prerequisite that the ring is aromatic, i.e. it comprises a cyclic system of six delocalized pi electrons. Monocyclic aromatic heterocycles are 5-membered or 6-membered rings and, in the case of a 5-membered ring, comprise one ring heteroatom selected from the series consisting of oxygen, sulfur and nitrogen, wherein this ring nitrogen carries an exocyclic group like a hydrogen atom or a substituent, and optionally one or more further ring nitrogen atoms, and, in the case of a 6-membered ring, comprise one or more nitrogen atoms as ring heteroatoms, but no oxygen atoms and sulfur atoms as ring heteroatoms. Unless specified otherwise in the definition of the group, heterocyclic groups can be bonded via any suitable ring atom, i.e. any ring atom which can carry a hydrogen atom or a substituent, including ring carbon atoms and ring nitrogen atoms. In one embodiment of the invention, any of the heterocyclic groups occurring in the compounds of the formula I in any of its occurrences, is independently of its other occurrences and independently of any other heterocyclic group, bonded via a ring carbon atom, and in another embodiment via a ring nitrogen atom, if applicable and not specified otherwise. In substituted heterocyclic groups, the substituents can be located in any positions.

The number of ring heteroatoms which can be present in a heterocyclic group in the compounds of the formula I, the number of cycles, i.e. whether the heterocyclic group can be monocyclic and/or bicyclic, the number of ring members which can be present, and the degree of saturation, i.e. whether the heterocyclic group is saturated and does not contain a double bond within the ring, or whether it is partially unsaturated and contains one or more, for example one or two, double bonds within the ring but is not aromatic, or whether it is aromatic and thus contains two double bonds within the ring in the case of a 5-membered monocyclic aromatic heterocycle, three double bonds within the ring in the case of a 6-membered monocyclic aromatic heterocycle, four double bonds within the ring in the case of 9-membered bicyclic aromatic heterocycle, and five double bonds within the ring in the case of 10-membered aromatic heterocycle, is specified in the definitions of the individual groups in the compounds of the formula I. The two cycles in bicyclic heterocyclic groups can have one, two or more ring atoms in common and can be fused or form a bridged bicycle or a spirocycle. As examples of heterocyclic ring systems, from which heterocyclic groups in the compounds of the formula I can be derived, and from any one or more of which any of the heterocyclic groups in the compounds of the formula I is selected in one embodiment of the invention, provided that the ring system is comprised by the definition of the group, oxetane, thietane, azetidine, furan, tetrahydrofuran, thiophene, tetrahydrothiophene, pyrrole, pyrroline, pyrrolidine, 1,3-dioxole, 1,3-dioxolane, isoxazole ([1,2]oxazole), isoxazoline, isoxazolidine, oxazole ([1,3]oxazole), oxazoline, oxazolidine, isothiazole ([1,2]thiazole), isothiazoline, isothiazolidine, thiazole ([1,3]thiazole), thiazoline, thiazolidine, pyrazole, pyrazoline, pyrazolidine, imidazole, imidazoline, imidazolidine, [1,2,3]triazole, [1,2,4]triazole, [1,2,4]oxadiazole, [1,3,4]oxadiazole, 1,2,5-oxadiazole, [1,2,4]thiadiazole, pyran, tetrahydropyran, thiopyran, tetrahydrothiopyran, 2,3-dihydro[1,4]dioxine, 1,4-dioxane, pyridine, 1,2,5,6-tetrahydropyridine, piperidine, morpholine, thiomorpholine, piperazine, pyridazine, pyrimidine, pyrazine, [1,2,4]triazine, oxepane, thiepane, azepane, [1,3]diazepane, [1,4]diazepane, [1,4]oxazepane, [1,4]thiazepane, azocane, 3-azabicyclo[3.1.0]hexane, octahydrocyclopenta[b]pyrrole, octahydrocyclopenta[c]pyrrole, 2-azaspiro[4.4]nonane, 7-azabicyclo[2.2.1]heptane, 2,7-diazaspiro[4.4] nonane, benzofuran, isobenzofuran, benzothiophene (benzo[b]thiophene), 1H-indole, 2,3-dihydro-1H-indole, octahydroindole, 2H-isoindole, octahydroisoindole, benzo[1,3]dioxole, benzoxazole, benzthiazole, benzisothiazole, 1H-benzimidazole, imidazo[1,2-a]pyridine, isothiazolo[5,4-b]pyridine, chroman, isochroman, thiochroman, benzo[1,4]dioxane, 3,4-dihydro-2H-benzo[1,4]oxazine, 3,4-dihydro-2H-benzo[1,4]thiazine, 2-azaspiro[4.5]decane, 3-azabicyclo[3.2.2]nonane, quinoline, 1,2,3,4-tetrahydroquinoline, 5,6,7,8-tetrahydroquinoline, isoquinoline, 1,2,3,4,-tetrahydroisoquinoline, 5,6,7,8-tetrahydroisoquinoline, 2,7-diazaspiro[4.5]decane, 2,8-diazaspiro[4.5]decane, cinnoline, quinazoline, quinoxaline, phthalazine and [1,8]naphthyridine may be mentioned, which are all optionally substituted in any suitable positions as specified in the definition of the respective group in the compounds of the formula I, wherein the degree of unsaturation indicated above is by way of example only, and in the individual groups also ring systems with a higher or lower degree of saturation, or hydrogenation, or of unsaturation can be present as specified in the definition of the groups in the compounds of the formula I.

As mentioned, the heterocyclic groups can be bonded via any suitable ring atom, unless specified otherwise. For example, among others can an oxetane and a thietane ring be bonded via positions 2 and 3, an azetidine ring via positions 1, 2 and 3, a furan ring, a tetrahydrofuran ring, a thiophene ring and a tetrahydrothiophene via positions 2 and 3, a pyrrole ring and a pyrrolidine ring via positions 1, 2 and 3, an isoxazole ring and an isothiazole ring via positions 3, 4 and 5, a pyrazole ring via positions 1, 3, 4 and 5, an oxazole ring and a thiazole ring via positions 2, 4 and 5, an imidazole ring and an imidazolidine ring via positions 1, 2, 4 and 5, a tetrahydropyran and a tetrahydrothiopyran ring via positions 2, 3 and 4, a 1,4-dioxane ring via position 2, a pyridine ring via positions 2, 3 and 4, a piperidine ring via positions 1, 2, 3 and 4, a morpholine ring and a thiomorpholine ring via positions 2, 3 and 4, a piperazine ring via positions 1 and 2, a pyrimidine ring via positions 2, 4 and 5, a pyrazine ring via position 2, an azepane ring via positions 1, 2, 3 and 4, a 3-azabicyclo[3.1.0]hexane ring via positions 3 and 6, an octahydrocyclopenta[b]pyrrole and an octahydrocyclopenta[c]pyrrole ring via position 1, a 2-azaspiro[4.4]nonane ring via position 2, a 7-azabicyclo[2.2.1]heptane ring via position 7, a benzofuran ring and a benzothiophene ring via positions 2, 3, 4, 5, 6 and 7, a 1H-indole ring, a 2,3-dihydro-1H-indole and an octahydroindole ring via positions 1, 2, 3, 4, 5, 6 and 7, a benzo[1,3]dioxole ring via positions 4, 5, 6 and 7, a benzoxazole ring and a benzthiazole ring via positions 2, 4, 5, 6 and 7, a 1H-benzimidazole ring via positions 1, 2, 4, 5, 6 and 7, an imidazo[1,2-a]pyridine ring via positions 2 and 3, a benzo[1,4]dioxane ring via positions 5, 6, 7 and 8, a 3-azabicyclo[3.2.2]nonane ring via position 3, a quinoline ring via positions 2, 3, 4, 5, 6, 7 and 8, a 1,2,3,4-tetrahydroquinoline ring via positions 1, 5, 6, 7 and 8, a 5,6,7,8-tetrahydroquinoline via positions 2, 3 and 4, an isoquinoline ring via positions 1, 3, 4, 5, 6, 7 and 8, a 1,2,3,4-tetrahydroisoquinoline ring via positions 2, 5, 6, 7 and 8, a 5,6,7,8-tetrahydroisoquinoline ring via positions 1, 3, 4 and 5, a 2,7-diazaspiro[4.5]decane ring via positions 2 and 7, a 2,8-diazaspiro[4.5]decane ring via positions 2 and 8, for example, wherein the resulting residues of the heterocyclic groups are all optionally substituted in any suitable positions as specified in the definition of the respective group in the compounds of the formula I.

Halogen is fluorine, chlorine, bromine or iodine. In one embodiment of the invention, in any of its occurrences halogen is fluorine, chlorine or bromine, in another embodiment fluorine or chlorine, in another embodiment fluorine, in another embodiment chorine, where all occurrences of halogen are independent of each other.

An oxo group, i.e. a doubly bonded oxygen atom, when bonded to a carbon atom, replaces two hydrogen atoms on a carbon atom of the parent system. Thus, if a $CH_2$ group is substituted by oxo, it becomes a carbonyl group (C(O), C=O). Oxo groups can also occur on sulfur atoms, such as on ring sulfur atoms in saturated and partially unsaturated heterocycles in which generally, besides a ring sulfur atom, also an S(O) group (S(=O)) and an $S(O)_2$ group (S(=O)$_2$) can be present as hetero ring members. An oxo group cannot occur as a substituent on a carbon atom in an aromatic ring such as in a phenyl group. Further, also the oxygen atom which is bonded to a nitrogen atom in an N-oxide moiety, can be regarded as an oxo group. The oxygen atom in an N-oxide moiety can also be regarded as a hydroxy group which is deprotonated to a negatively charged oxy group, this negatively charged group together with the positively charged nitrogen atom carrying it forming an internal salt (betaine, zwitterion). If the definition of a group comprises suitable nitrogen heterocycles such as pyridine ring, quinoline rings, isoquinoline rings or isothiazolo[5,4-b]pyridine rings, for example, and the group can be substituted by an oxo substituent or hydroxy substituent, such substituent can also be present on a ring nitrogen atom, and the N-oxide of the nitrogen heterocycle thus is also comprised. N-oxide moieties in aromatic rings may be represented by structural elements such as =N(=O)— or =N(—O)— or =N$^+$(O$^-$)- or =N(O)—.

The present invention comprises all stereoisomeric forms of the compounds of the formula I, for example all enantiomers and diastereomers including cis/trans isomers. The invention likewise comprises mixtures of two or more stereoisomeric forms, for example mixtures of enantiomers and/or diastereomers including cis/trans isomers, in all ratios. Asymmetric centers contained in the compounds of the formula I can all independently of each other have S configuration or R configuration. The invention relates to enantiomers, both the levorotatory and the dextrorotatory antipode, in enantiomerically pure form and essentially enantiomerically pure form, for example with a molar ratio of the two enantiomers of 98:2, or 99:1, or greater, and in the form of their racemate, i.e. a mixture of the two enantiomers in molar ratio of 1:1, and in the form of mixtures of the two enantiomers in all ratios. The invention likewise relates to diastereomers in the form of pure and essentially pure diastereomers and in the form of mixtures of two or more diastereomers in all ratios. The invention also comprises all cis/trans isomers of the compounds of the formula I in pure form and essentially pure form, for example with a molar ratio of the cis/trans isomers of 98:2, or 99:1, or greater, and in the form of mixtures of the cis isomer and the trans isomer in all ratios. Cis/trans isomerism can occur in substituted rings. The preparation of individual stereoisomers, if desired, can be carried out by resolution of a mixture according to customary methods, for example, by chromatography or crystallization, or by use of stereochemically uniform starting compounds in the synthesis, or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. For example, in the case of a compound of the formula I containing an asymmetric center the individual enantiomers can be prepared by preparing the racemate of the compound of the formula I and resolving it into the enantiomers by high pressure liquid chromatography on a chiral phase according to standard procedures, or resolving the racemate of any intermediate in the course of its synthesis by such chromatography or by crystallization of a salt thereof with an optically active amine or acid and converting the enantiomers of the intermediate into the enantiomeric forms of the final compound of the formula I, or by performing an enantioselective reaction in the course of the synthesis. The invention also comprises all tautomeric forms of the compounds of the formula I.

If the compounds of the formula I comprise one or more acidic or basic groups, for example basic heterocyclic groups, the corresponding physiologically or toxicologically acceptable salts are also included in the invention, especially the pharmaceutically acceptable salts. The compounds of the formula I may thus be deprotonated on an acidic group and be used for example as alkali metal salts or as ammonium salts. Compounds of the formula I comprising at least one basic group may also be prepared and used in the form of their acid addition salts, for example in the form of pharmaceutically acceptable salts with inorganic acids and organic acids. Salts can in general be prepared from acidic and basic compounds of the formula I by reaction with an acid or base in a solvent or diluent according to customary procedures. If the compounds of the formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical, but are suitable as intermediates for chemical reactions or for the preparation of physiologically acceptable salts, for example by means of anion exchange or cation exchange.

In one embodiment of the invention, the group X in the compounds of the formula I is =N— and the compound of the formula I thus is a compound of the formula Ia, i.e., in this embodiment the pyridine ring of the isothiazolo[5,4-b]pyridine ring system contains a free nitrogen atoms or, in case of the formation of an acid addition salt on this nitrogen atom, a protonated nitrogen atom. In another embodiment of the invention, the group X in the compounds of the formula I is =N(O)— and the compound of the formula I thus is a compound of the formula Ib, i.e., in this embodiment the pyridine ring of the isothiazolo[5,4-b]pyridine ring system contains a nitrogen atom which has been converted into the N-oxide. In the compounds of the formulae Ia and Ib the groups R1, R2, R3, R10 and R11 are defined as in the compounds of the formula I or in any of the embodiments defined herein.

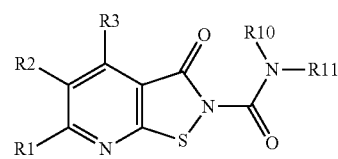

Ia

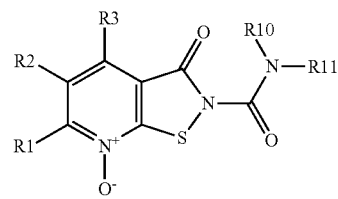

Ib

In one embodiment of the invention, R1, R2 and R3 are independently of one another selected from the series consisting of hydrogen, halogen, $(C_1-C_4)$-alkyl, nitro, cyano, $(C_1-C_4)$-alkyl-O—C(O)— and R4-N(R5)-C(O)—, in another embodiment from the series consisting of hydrogen, halogen, $(C_1-C_4)$-alkyl, cyano, $(C_1-C_4)$-alkyl-O—C(O)— and R4-N(R5)-C(O)—, in another embodiment from the series consisting of hydrogen, halogen, $(C_1-C_4)$-alkyl, nitro and cyano, in another embodiment from the series consisting of hydrogen, halogen, $(C_1-C_4)$-alkyl and cyano, in another embodiment from the series consisting of hydrogen, halogen and $(C_1-C_4)$-alkyl, in another embodiment from the series consisting of hydrogen, halogen and cyano, in another embodiment from the series consisting of hydrogen, $(C_1-C_4)$-alkyl and cyano, in another embodiment from the series consisting of hydrogen and halogen, in another embodiment from the series consisting of hydrogen and cyano, in another embodiment from the series consisting of hydrogen and $(C_1-C_4)$-alkyl, and in another embodiment R1, R2 and R3 all are hydrogen. In one embodiment, one or two of the groups R1, R2 and R3 are independently of one another selected from any of the series specified before, and the other of the groups R1, R2 and R3 are hydrogen, and in another embodiment one of the groups R1, R2 and R3 is selected from any of the series specified before, and the other of the groups R1, R2 and R3 are hydrogen. In one embodiment, R1 and R3 are independently of one another selected from any of the series specified before and R2 is selected from the series consisting of hydrogen, halogen and cyano, in another embodiment from the series consisting of hydrogen and halogen, in another embodiment from the series consisting of hydrogen and cyano, and in another embodiment is hydrogen. In one embodiment, R1 and R3 are hydrogen and R2 is cyano. In one embodiment, R2 is selected from any of the series specified before, and R1 and R3 are independently of one another are selected from the series consisting of hydrogen, halogen and $(C_1-C_4)$-alkyl, in another embodiment from the series consisting of hydrogen and halogen, in another embodiment from the series consisting of hydrogen and $(C_1-C_4)$-alkyl, and in another embodiment both are hydrogen.

In one embodiment of the invention, a heterocyclic group Het1 present in R4 is a monocyclic 4-membered to 7-membered saturated group or 5-membered to 6-membered aromatic group, in another embodiment a monocyclic 4-membered to 7-membered saturated group, in another embodiment a 5-membered to 6-membered aromatic group, which comprises 1, 2 or 3, in another embodiment 1 or 2, in another embodiment 1, identical or different ring heteroatoms selected from the series consisting of nitrogen, oxygen and sulfur, in another embodiment from the series consisting of nitrogen and oxygen, in another embodiment from the series consisting of nitrogen and sulfur. In one embodiment, the number of substituents R8 which are optionally present in a group Het1 present in R4, is 1, 2, 3 or 4, in another embodiment 1, 2 or 3, in another embodiment 1 or 2, in another embodiment 1.

In one embodiment, R4 is selected from the series consisting of hydrogen, $(C_1-C_4)$-alkyl, $(C_3-C_7)$-cycloalkyl, $(C_3-C_7)$-cycloalkyl-$(C_1-C_4)$-alkyl-, phenyl and phenyl-$(C_1-C_4)$-alkyl-, in another embodiment from the series consisting of hydrogen, $(C_1-C_4)$-alkyl, $(C_3-C_7)$-cycloalkyl, $(C_3-C_7)$-cycloalkyl-$(C_1-C_4)$-alkyl-, phenyl and Het1, in another embodiment from the series consisting of hydrogen, $(C_1-C_4)$-alkyl, $(C_3-C_7)$-cycloalkyl, $(C_3-C_7)$-cycloalkyl-$(C_1-C_4)$-alkyl- and phenyl, in another embodiment from the series consisting of hydrogen, $(C_1-C_4)$-alkyl, $(C_3-C_7)$-cycloalkyl and $(C_3-C_7)$-cycloalkyl-$(C_1-C_4)$-alkyl-, in another embodiment from the series consisting of hydrogen and $(C_1-C_4)$-alkyl, and in another embodiment it is hydrogen, wherein all groups are optionally substituted as specified in the definition of the compounds of the formula I or in any embodiment specified herein.

In one embodiment of the invention, R5, R6 and R7 are independently of one another selected from the series consisting of hydrogen and $(C_1-C_4)$-alkyl, and in another embodiment they are hydrogen.

In one embodiment of the invention, substituents R8 which can occur on groups Het1 present in R4, are selected from the series consisting of halogen, $(C_1-C_4)$-alkyl, hydroxy, oxo, $(C_1-C_4)$-alkyl-O— and cyano in case of a saturated or partially unsaturated group Het1, and from the series consisting of halogen, $(C_1-C_4)$-alkyl, hydroxy, $(C_1-C_4)$-alkyl-O— and cyano in case of an aromatic group Het1. In one embodiment, R8 is selected from the series consisting of halogen, $(C_1-C_4)$-alkyl, hydroxy, $(C_1-C_4)$-alkyl-O— and cyano, in another embodiment from the series consisting of halogen, $(C_1-C_4)$-alkyl, $(C_1-C_4)$-alkyl-O— and cyano, in another embodiment from the series consisting of halogen, $(C_1-C_4)$-alkyl and $(C_1-C_4)$-alkyl-O—, in another embodiment from the series consisting of halogen and $(C_1-C_4)$-alkyl.

In one embodiment of the invention, R10 is selected from the series consisting of hydrogen, $(C_1-C_4)$-alkyl, $(C_3-C_7)$-cycloalkyl and $(C_3-C_7)$-cycloalkyl-$(C_1-C_4)$-alkyl-, in another embodiment from the series consisting of hydrogen, $(C_1-C_4)$-alkyl and $(C_1-C_4)$-alkyl-O—$(C_1-C_4)$-alkyl-, in another embodiment from the series consisting of hydrogen and $(C_1-C_4)$-alkyl, with the proviso that R10 can only be hydrogen if X is =N(O)—, wherein in all these embodiments R11 is as defined for the compounds of the formula I or in any embodiment specified herein and R10 and R11 together with the nitrogen atom carrying them can form a heterocycle. In one embodiment, R10 is hydrogen and, in view of the proviso that R10 can only be hydrogen if X is =N(O)—, the compounds of this embodiment thus are compounds of the formula Ic, in which the groups R1, R2, R3 and R11 are defined as in the compounds of the formula I or in any of the embodiments defined herein.

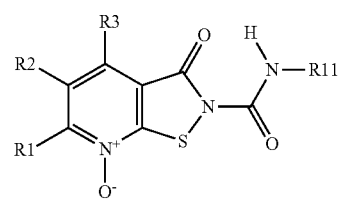

Ic

In one embodiment, R10 is selected from the series consisting of $(C_1-C_4)$-alkyl, $(C_3-C_7)$-cycloalkyl, $(C_3-C_7)$-cycloalkyl-$(C_1-C_4)$-alkyl- and $(C_1-C_4)$-alkyl-O—$(C_1-C_4)$-alkyl-, in another embodiment from the series consisting of $(C_1-C_4)$-alkyl, $(C_3-C_7)$-cycloalkyl and $(C_3-C_7)$-cycloalkyl-$(C_1-C_4)$-alkyl-, in another embodiment from the series consisting of $(C_1-C_4)$-alkyl, $(C_3-C_7)$-cycloalkyl and $(C_1-C_4)$-alkyl-O—$(C_1-C_4)$-alkyl-, in another embodiment from the series consisting of $(C_1-C_4)$-alkyl and $(C_3-C_7)$-cycloalkyl, in another embodiment from the series consisting of $(C_1-C_4)$-alkyl and $(C_1-C_4)$-alkyl-O—$(C_1-C_4)$-alkyl-, in another embodiment R10 is $(C_1-C_4)$-alkyl, in another embodiment $(C_1-C_3)$-alkyl, in another embodiment $(C_1-C_2)$-alkyl, in another embodiment methyl, wherein in all these embodiments R11 is as defined for the compounds of the formula I or in any embodiment specified herein and R10 and R11 together with the nitrogen atom carrying them can form a heterocycle.

In one embodiment of the invention, a heterocyclic group Het2 representing R11 is a monocyclic 5-membered to 7-membered, in another embodiment a 5-membered to 6-membered, in another embodiment a 6-membered, in another embodiment a 4-membered saturated group bonded via a ring carbon atom, which comprises 1 or 2, in another embodiment 1, identical or different ring heteroatoms selected from the series consisting of nitrogen, oxygen and sulfur, in another embodiment from the series consisting of nitrogen and oxygen, in another embodiment from the series consisting of nitrogen and sulfur. In another embodiment, ring heteroatoms in a group Het2 representing R11 are nitrogen atoms, in another embodiment oxygen atoms. In one embodiment, the number of substituents R14 which are optionally present in a group Het2 representing R11, is 1, 2, 3, 4, 5 or 6, in another embodiment 1, 2, 3, 4 or 5, in another embodiment 1, 2, 3 or 4, in another embodiment 1, 2 or 3, in another embodiment 1 or 2, in another embodiment 1. In one embodiment, R11 is selected from the series consisting of $(C_1-C_4)$-alkyl which is optionally substituted by one or more identical or different substituents R12, and Het2 which is optionally substituted by one or more identical or different substituents R14 and wherein Het2 is bonded via a ring carbon atom, and in another embodiment R11 is $(C_1-C_4)$-alkyl which is optionally substituted by one or more identical or different substituents R12, wherein in all these embodiments R10 is as defined for the compounds of the formula I or in any embodiment specified herein and R10 and R11 together with the nitrogen atom carrying them can form a heterocycle. In one embodiment, the number of substituents R12 which are optionally present in an alkyl group representing R11, is 1, 2, 3, 4, 5 or 6, in another embodiment 1, 2, 3 or 4, in another embodiment 1, 2 or 3, in another embodiment 1 or 2, in another embodiment 1. In one embodiment, the number of substituents R13 which are optionally present in a cycloalkyl group representing R11, is 1, 2, 3 or 4, in another embodiment 1, 2 or 3, in another embodiment 1 or 2, in another embodiment 1.

The monocyclic or bicyclic heterocycle which can be formed by R10 and R11 together with the nitrogen atom carrying them, can be 4-membered, 5-membered, 6-membered, 7-membered, 8-membered, 9-membered, 10-membered, 11-membered or 12-membered. In one embodiment of the invention the heterocycle which can be formed by R10 and R11 together with the nitrogen atom carrying them, is a 4-membered to 10 membered monocyclic or bicyclic heterocycle, in another embodiment a 5-membered to 10-membered monocyclic or bicyclic heterocycle, in another embodiment a 4-membered to 7-membered monocyclic heterocycle or a 6-membered to 12-membered bicyclic heterocycle, in another embodiment a 4-membered to 7-membered monocyclic heterocycle, in another embodiment a 5-membered to 6-membered monocyclic heterocycle, in another embodiment a 6-membered heterocycle. As mentioned above with respect to heterocycles in general, the two rings in a bicyclic heterocycle which can be formed by R10 and R11 together with the nitrogen atom carrying them can have one, two or more ring atoms in common and can be fused or form a bridged bicycle or a spirocycle. If R10 and R11 together with the nitrogen atom carrying them form a partially unsaturated heterocycle, i.e. a monocyclic or bicyclic heterocycle which is unsaturated but in the ring which comprises the nitrogen atom carrying R10 and R11 is not aromatic, it can contain 1, 2, 3 or 4 double bonds, for example, and in one embodiment contains 1, 2 or 3 double bonds, in another embodiment 1 or 2 double bonds, in another embodiment 1 double bond, within the ring system, wherein the number of double bonds depends on the kind of the ring system and ring size. In a bicyclic ring, the double bonds can be present in one of the rings or both of them. In one embodiment, the heterocycle which can be formed by R10 and R11 together with the nitrogen atom carrying them, comprises 0 or 1, in another embodiment 0 (zero), in another embodiment 1, further ring heteroatom which is selected from the series consisting of nitrogen, oxygen and sulfur, in addition to the nitrogen atom carrying R10 and R11. In one embodiment, further ring heteroatoms in a heterocycle which can be formed by R10 and R11 together with the nitrogen atom carrying them, are selected from the series consisting of nitrogen and oxygen, in another embodiment from the series consisting of nitrogen and sulfur, in another embodiment they are nitrogen atoms, and in another embodiment they are oxygen atoms. In one embodiment of the invention, a heterocycle which can be formed by R10 and R11 together with the nitrogen atom carrying them, comprises 0 or 1 further ring heteroatom which is selected from the series consisting of nitrogen and oxygen and in another embodiment is a nitrogen atom, in addition to the nitrogen atom which carries R10 and R11 and via which the heterocycle is bonded. In one embodiment, the number of substituents R30 which are optionally present on ring carbon atoms of a heterocycle formed by R10 and R11 together with the nitrogen atom carrying them, is 1, 2, 3 or 4, in another embodiment 1, 2 or 3, in another embodiment 1 or 2, in another embodiment 1, wherein substituents R30 can be present on one or more ring carbon atoms and the maximum number of substituents R30 on an individual ring carbon atom is 2. In one embodiment, the number of optional substituents R40 which can be present on further ring nitrogen atoms in a heterocycle which can be formed by R10 and R11 together with the nitrogen atom carrying them, is 1 or 2, in another embodiment it is 1. In one embodiment of the invention, a heterocycle which can be formed by R10 and R11 together with the nitrogen atom carrying them, comprises 1 further ring heteroatom which is a nitrogen atom carrying a substituent R40.

As examples of heterocyclic groups, from any one or more of which the heterocyclic group which can be formed by R10 and R11 together with the nitrogen atom carrying them, is selected in one embodiment of the invention, the groups of the following formulae may be mentioned,

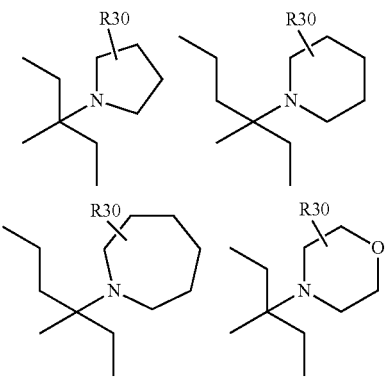

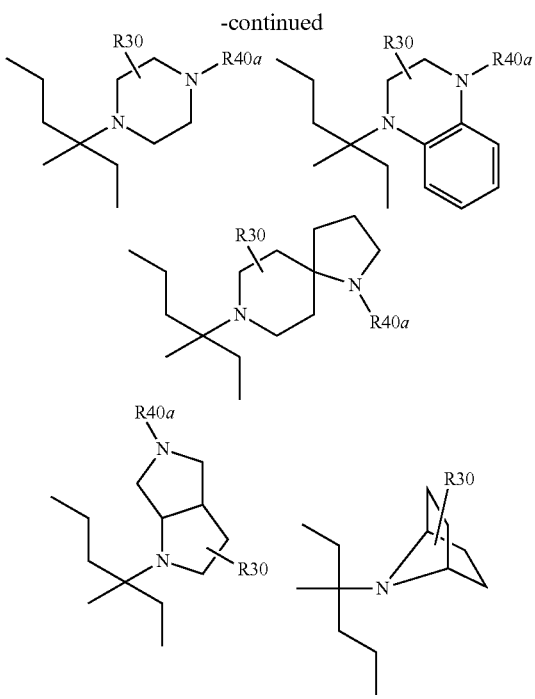

in which the line crossed with the symbol ⁓ represents the free bond via which the group is bonded to the carbon atom of the carbonyl group attached to the 2-position of the isothiazolo[5,4-b]pyridine ring system. The group R30 depicted in these formulae is defined as the group R30 in the compounds of the formula I or in any embodiment specified herein. The bond originating at the groups R30, which bond is not directed to a specific atom, indicates that these heterocyclic groups are optionally substituted on ring carbon atoms by one or more identical or different substituents R30 which can be present in any positions. The group R40a depicted in these formulae is defined as the group R40 defined for the compounds of the formula I or in any embodiment specified herein, and can additionally be hydrogen. By the groups R40a it is indicated that the further ring nitrogen atom which is present in the respective heterocycles, can be unsubstituted, i.e. carry a hydrogen atom, or substituted by a substituent R40.

In one embodiment of the invention, the groups R10 and R11 together with the nitrogen atom carrying them form a heterocycle which is defined as specified in the definition of the compounds of the formula I or in any embodiment specified herein, and in this embodiment R10 and R11 thus do not have their individual meanings. In another embodiment, the groups R10 and R11 together with the nitrogen atom carrying them form a heterocycle which is selected from the series consisting of pyrrolidine, piperidine, morpholine and piperazine, in another embodiment from the series consisting of piperidine, morpholine and piperazine, in another embodiment from the series consisting of pyrrolidine, piperidine and piperazine, in another embodiment from the series consisting of piperidine and piperazine, and in another embodiment it is a piperazine ring, which heterocycles are all bonded via a ring nitrogen atom and are optionally substituted on ring carbon atoms by one or more identical or different substituents R30, and wherein the further ring nitrogen atom in the piperazine ring is optionally substituted by a substituent R40 and in another embodiment is substituted by a substituent R40. The compounds of the latter embodiment may be represented by the formula Id, in which R1, R2, R3, R30, R40 and X are defined as in compounds of the formula I or in any embodiment specified herein, and the bond originating at the group R30, which is not directed to a specific atom, indicates that the piperazine ring is optionally substituted on ring carbon atoms by one or more identical or different substituents R30 which can be present in any positions.

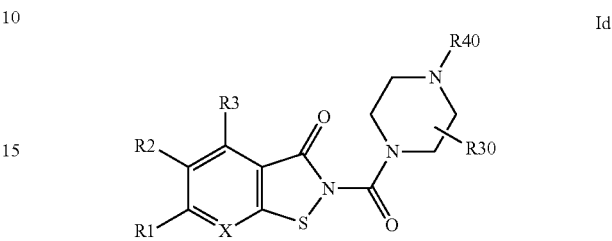

The monocyclic or bicyclic group Het3, which can represent R12, can be 4-membered, 5-membered, 6-membered, 7-membered, 8-membered, 9-membered, 10-membered, 11-membered or 12-membered. In one embodiment of the invention Het3 is a 4-membered to 10 membered monocyclic or bicyclic heterocycle, in another embodiment a 5-membered to 10-membered monocyclic or bicyclic heterocycle, in another embodiment a 4-membered to 7-membered monocyclic heterocycle or a 6-membered to 12-membered bicyclic heterocycle, in another embodiment a 5-membered to 7-membered monocyclic heterocycle or a 9-membered to 12-membered bicyclic heterocycle, in another embodiment a 5-membered to 7-membered monocyclic heterocycle or a 9-membered to 10-membered bicyclic heterocycle, in another embodiment a 4-membered to 7-membered monocyclic heterocycle, in another embodiment a 5-membered to 6-membered monocyclic heterocycle, in another embodiment a 6-membered monocyclic heterocycle. As mentioned above with respect to heterocycles in general, the two rings in a bicyclic group Het3 can have one, two or more ring atoms in common and can be fused or form a bridged bicycle or a spirocycle. If Het3 is a partially unsaturated heterocycle, i.e. a monocyclic or bicyclic heterocycle which is unsaturated but in the ring via which Het3 is bonded is not aromatic, it can contain 1, 2, 3 or 4 double bonds, for example, and in one embodiment contains 1, 2 or 3 double bonds, in another embodiment 1 or 2 double bonds, in another embodiment 1 double bond, within the ring system, wherein the number of double bonds depends on the kind of the ring system and ring size. In a bicyclic ring, the double bonds can be present in one of the rings or both of them. Monocyclic and bicyclic rings Het3 can also be aromatic, i.e. comprise a cyclic system of six delocalized pi electrons in 5-membered or 6-membered rings. In one embodiment, Het3 comprises 1 or 2, in another embodiment 1, identical or different ring heteroatoms which are selected from the series consisting of nitrogen, oxygen and sulfur. In one embodiment, the ring heteroatoms in Het3 are selected from the series consisting of nitrogen and oxygen, in another embodiment from the series consisting of nitrogen and sulfur, in another embodiment they are nitrogen atoms, and in another embodiment they are oxygen atoms. A group Het3 representing R12 can be bonded via any suitable ring carbon atom or ring nitrogen atom. In one embodiment, Het3 representing R12 is bonded via a ring carbon atom, in another embodiment via a ring nitrogen atom. In one embodiment, the number of substituents R19 which are optionally present on a group Het3 representing R12, and likewise, but independent thereof, the number of substituents R19 which are optionally present on a phenyl group representing R12, is 1, 2, 3 or 4, in another embodiment 1, 2 or 3, in another embodiment 1 or 2, in another embodiment 1.

In one embodiment of the invention, R12 is selected from the series consisting of phenyl, Het3, hydroxy, $(C_1-C_4)$-alkyl-O—, $(C_1-C_4)$-alkyl-C(O)—O—, R15-N(R16)- and R17-C(O)—N(R18)-, in another embodiment from the series consisting of phenyl, Het3, hydroxy, $(C_1-C_4)$-alkyl-O—, R15-N(R16)- and R17-C(O)—N(R18)-, in another embodiment from the series consisting of phenyl, hydroxy, $(C_1-C_4)$-alkyl-O—, R15-N(R16)- and R17-C(O)—N(R18)-, in another embodiment from the series consisting of Het3, hydroxy, $(C_1-C_4)$-alkyl-O—, R15-N(R16)- and R17-C(O)—N(R18)-, in another embodiment from the series consisting of phenyl, Het3, hydroxy and $(C_1-C_4)$-alkyl-O—, in another embodiment from the series consisting of Het3, hydroxy and $(C_1-C_4)$-alkyl-O—, in another embodiment from the series consisting of Het3, R15-N(R16)- and R17-C(O)—N(R18)-, in another embodiment from the series consisting of hydroxy, $(C_1-C_4)$-alkyl-O—, R15-N(R16)- and R17-C(O)—N(R18)-, in another embodiment from the series consisting of phenyl, Het3, $(C_1-C_4)$-alkyl-O—, R15-N(R16)- and R17-C(O)—N(R18)-, in another embodiment from the series consisting of Het3, $(C_1-C_4)$-alkyl-O—, R15-N(R16)- and R17-C(O)—N(R18)-, in another embodiment from the series consisting of $(C_1-C_4)$-alkyl-O—, R15-N(R16)- and R17-C(O)—N(R18)-, in another embodiment from the series consisting of phenyl and Het3, and in another embodiment R12 is Het3, wherein in all embodiment phenyl and Het3 are independently of one another optionally substituted by one or more identical or different substituents R19. In one embodiment, the total number of cycloalkyl groups, phenyl groups and Het3 groups representing the substituents R12 which are optionally present on an alkyl group representing R11, is 1 or 2, in another embodiment 1.

In one embodiment of the invention, R13 is selected from the series consisting of hydroxy, $(C_1-C_4)$-alkyl-O— and cyano-, in another embodiment from the series consisting of hydroxy and $(C_1-C_4)$-alkyl-O—, in another embodiment from the series consisting of hydroxy and cyano-, and in another embodiment R13 is cyano.

In one embodiment of the invention, R14 is selected from the series consisting of fluorine, $(C_1-C_4)$-alkyl, hydroxy, $(C_1-C_4)$-alkyl-C(O)—O—, HO—$(C_1-C_4)$-alkyl-, $(C_1-C_4)$-alkyl-C(O)—O—$(C_1-C_4)$-alkyl- and $(C_1-C_4)$-alkyl-C(O)—, in another embodiment from the series consisting of $(C_1-C_4)$-alkyl, hydroxy, $(C_1-C_4)$-alkyl-C(O)—O—, HO—$(C_1-C_4)$-alkyl-, $(C_1-C_4)$-alkyl-C(O)—O—$(C_1-C_4)$-alkyl- and $(C_1-C_4)$-alkyl-C(O)—, in another embodiment from the series consisting of $(C_1-C_4)$-alkyl, hydroxy, $(C_1-C_4)$-alkyl-C(O)—O—, HO—$(C_1-C_4)$-alkyl- and $(C_1-C_4)$-alkyl-C(O)—O—$(C_1-C_4)$-alkyl-, in another embodiment from the series consisting of hydroxy, $(C_1-C_4)$-alkyl-C(O)—O—, HO—$(C_1-C_4)$-alkyl- and $(C_1-C_4)$-alkyl-C(O)—O—$(C_1-C_4)$-alkyl-, in another embodiment from the series consisting of $(C_1-C_4)$-alkyl-C(O)—O— and $(C_1-C_4)$-alkyl-C(O)—O—$(C_1-C_4)$-alkyl-.

In one embodiment of the invention, R15, R16 and R18 are independently of one another selected from the series consisting of hydrogen and $(C_1-C_4)$-alkyl, in another embodiment from the series consisting of hydrogen and $(C_1-C_2)$-alkyl, and in another embodiment they are hydrogen.

In one embodiment of the invention, R17 is selected from the series consisting of $(C_1-C_4)$-alkyl, $(C_3-C_7)$-cycloalkyl and $(C_3-C_7)$-cycloalkyl-$(C_1-C_4)$-alkyl-, in another embodiment from the series consisting of $(C_1-C_4)$-alkyl and $(C_3-C_7)$-cycloalkyl, and in another embodiment R17 is $(C_1-C_4)$-alkyl.

In one embodiment of the invention, R19 is selected from the series consisting of halogen, $(C_1-C_4)$-alkyl, hydroxy, $(C_1-C_4)$-alkyl-O—, $(C_1-C_4)$-alkyl-C(O)—O— and cyano, in another embodiment from the series consisting of halogen, $(C_1-C_4)$-alkyl, $(C_1-C_4)$-alkyl-O— and cyano, in another embodiment from the series consisting of halogen, $(C_1-C_4)$-alkyl and $(C_1-C_4)$-alkyl-O—, in another embodiment from the series consisting of halogen, $(C_1-C_4)$-alkyl, hydroxy, $(C_1-C_4)$-alkyl-O— and $(C_1-C_4)$-alkyl-C(O)—O—, in another embodiment from the series consisting of halogen, $(C_1-C_4)$-alkyl, hydroxy and $(C_1-C_4)$-alkyl-O—, in another embodiment from the series consisting of $(C_1-C_4)$-alkyl, hydroxy, $(C_1-C_4)$-alkyl-O— and $(C_1-C_4)$-alkyl-C(O)—O—, in another embodiment from the series consisting of hydroxy, $(C_1-C_4)$-alkyl-O— and $(C_1-C_4)$-alkyl-C(O)—O—, in another embodiment from the series consisting of hydroxy and $(C_1-C_4)$-alkyl-C(O)—O—, and in another embodiment R19 is hydroxy, wherein substituents R19 present on phenyl groups representing R12 and on Het3 groups representing R12 are defined independent of one another.

In one embodiment of the invention, R20, R21 and R22 are independently of one another selected from the series consisting of hydrogen and $(C_1-C_2)$-alkyl, and in another embodiment they are hydrogen.

In one embodiment of the invention, a heterocyclic group Het2 representing R30 is a monocyclic 5-membered to 7-membered, in another embodiment a 5-membered to 6-membered, in another embodiment a 6-membered, in another embodiment a 5-membered, in another embodiment a 4-membered saturated group. Het2 representing R30 can be bonded via any suitable ring atom, and in one embodiment is bonded via a ring carbon atom and in another embodiment via a ring nitrogen atom. In one embodiment, Het2 representing R30 comprises one ring heteroatom. In one embodiment, the ring heteroatoms in a group Het2 representing R30 are identical or different ring heteroatoms selected from the series consisting of nitrogen and sulfur, in another embodiment from the series consisting of nitrogen and oxygen, in another embodiment from the series consisting of oxygen and sulfur, in another embodiment they nitrogen atoms, and in another embodiment they are oxygen atoms. In one embodiment, the number of substituents R36 which are optionally present in a group Het2 representing R30, is 1, 2, 3 or 4, in another embodiment 1, 2 or 3, in another embodiment 1 or 2, in another embodiment 1.

In one embodiment of the invention, R30 is selected from the series consisting of $(C_1-C_4)$-alkyl, Het2, hydroxy, oxo, R31-N(R32)-, $(C_1-C_4)$-alkyl-C(O)—, R33-O—C(O)— and R34-N(R35)-C(O)—, in another embodiment from the series consisting of $(C_1-C_4)$-alkyl, Het2, hydroxy, oxo, R31-N(R32)- and $(C_1-C_4)$-alkyl-C(O)—, in another embodiment from the series consisting of $(C_1-C_4)$-alkyl, hydroxy, oxo, R31-N(R32)- and $(C_1-C_4)$-alkyl-C(O)—, in another embodiment from the series consisting of $(C_1-C_4)$-alkyl, Het2, hydroxy, oxo and R31-N(R32)-, in another embodiment from the series consisting of $(C_1-C_4)$-alkyl, hydroxy, oxo and R31-N(R32)-, in another embodiment from the series consisting of $(C_1-C_4)$-alkyl, hydroxy and R31-N(R32)-, in another embodiment from the series consisting of $(C_1-C_4)$-alkyl and R31-N(R32)-, in another embodiment from the series consisting of $(C_1-C_4)$-alkyl and hydroxy, wherein in all these embodiments Het2 is optionally substituted by one or more identical or different substituents R36. In one embodiment, the number of groups Het2 representing R30 which are optionally present as substituents on ring carbon atoms in a heterocycle formed by R10 and R11 together with the nitrogen atom carrying them, is one or two, in another embodiment one. In one embodiment, the number of oxo groups representing R30 which are optionally present as substituents on ring carbon atoms in a heterocycle formed by R10 and R11 together with the nitrogen atom carrying them, is one or two, in another embodiment one.

In one embodiment of the invention, R31, R32, R33, R34 and R35 are independently of one another selected from the series consisting of hydrogen and $(C_1-C_2)$-alkyl, and in another embodiment they are hydrogen.

In one embodiment of the invention, R36 is selected from the series consisting of $(C_1-C_4)$-alkyl, hydroxy and oxo, in another embodiment from the series consisting of $(C_1-C_4)$-alkyl and oxo, and in another embodiment R36 is $(C_1-C_4)$-alkyl. In one embodiment, the number of oxo substituents which are optionally present in a group Het2 representing R30 is 1 or 2, in another embodiment it is 1.

In one embodiment of the invention, a heterocyclic group Het1 representing R40 is a monocyclic 4-membered to 7-membered saturated or partially unsaturated group or 5-membered to 6-membered aromatic group, in another embodiment a monocyclic 4-membered to 7-membered saturated or partially unsaturated group, in another embodiment a 5-membered to 6-membered aromatic group, in another embodiment a 5-membered or 6-membered partially unsaturated or aromatic group, in another embodiment a 6-membered partially unsaturated or aromatic group, which comprises 1, 2 or 3, in another embodiment 2 or 3, in another embodiment 1 or 2, in another embodiment 1, identical or different ring heteroatoms selected from the series consisting of nitrogen, oxygen and sulfur, in another embodiment from the series consisting of nitrogen and oxygen, in another embodiment from the series consisting of nitrogen and sulfur. In one embodiment, the ring heteroatoms in a group Het1 representing R40 are nitrogen atoms. In one embodiment, the number of substituents R44 which are optionally present in a group Het1 present in R40, is 1, 2, 3 or 4, in another embodiment 1, 2 or 3, in another embodiment 1 or 2, in another embodiment 1.

The monocyclic or bicyclic group Het3 occurring in the group Het3-C(O)— which can represent R40, can be 4-membered, 5-membered, 6-membered, 7-membered, 8-membered, 9-membered, 10-membered, 11-membered or 12-membered. The explanations given above with respect to groups Het3 representing R12 apply correspondingly to such groups Het3 occurring in R40, if applicable. Thus, for example, in one embodiment of the invention a group Het3 occurring in R40 is a 4-membered to 10 membered monocyclic or bicyclic heterocycle, in another embodiment a 5-membered to 10-membered monocyclic or bicyclic heterocycle, in another embodiment a 4-membered to 7-membered monocyclic heterocycle or a 6-membered to 12-membered bicyclic heterocycle, in another embodiment a 5-membered to 7-membered monocyclic heterocycle or a 9-membered to 12-membered bicyclic heterocycle, in another embodiment a 5-membered to 7-membered monocyclic heterocycle or a 9-membered to 10-membered bicyclic heterocycle, in another embodiment a 4-membered to 7-membered monocyclic heterocycle, in another embodiment a 5-membered to 6-membered monocyclic heterocycle, in another embodiment a 6-membered monocyclic heterocycle. A group Het3 occurring in R40 is bonded via a ring carbon atom. In one embodiment, a group Het3 occurring in R40 is saturated or aromatic, in another embodiment it is saturated, in another embodiment it is aromatic. In one embodiment, Het3 comprises 1 or 2, in another embodiment 1, identical or different ring heteroatoms which are selected from the series consisting of nitrogen, oxygen and sulfur. In one embodiment, the ring heteroatoms in Het3 are selected from the series consisting of nitrogen and oxygen, in another embodiment from the series consisting of nitrogen and sulfur, in another embodiment they are nitrogen atoms, and in another embodiment they are oxygen atoms. In one embodiment, the number of substituents R48 which are optionally present on a group Het3 occurring in R40, i.e. in the Het3 part of the group Het3-C(O)—, is 1, 2, 3 or 4, in another embodiment 1, 2 or 3, in another embodiment 1 or 2, in another embodiment 1.

In one embodiment, the number of substituents R41 which are optionally present on a $(C_1-C_4)$-alkyl group representing R40, is 1, 2 or 3, in another embodiment 1 or 2, in another embodiment 1. In one embodiment, the number of substituents R42 which are optionally present on a $(C_3-C_7)$-cycloalkyl group representing R40, is 1, 2, 3 or 4, in another embodiment 1, 2 or 3, in another embodiment 1 or 2, in another embodiment 1. In one embodiment, the number of substituents R43 which are optionally present on a phenyl group representing R40, is 1, 2, 3 or 4, in another embodiment 1, 2 or 3, in another embodiment 1 or 2, in another embodiment 1. In one embodiment, the number of substituents R45 which are optionally present on a $(C_1-C_4)$-alkyl-C(O)— group representing R40, i.e. in the alkyl part of this group, is 1, 2 or 3, in another embodiment 1 or 2, in another embodiment 1. In one embodiment, the number of substituents R46 which are optionally present on a $(C_3-C_7)$-cycloalkyl-C(O)— group representing R40, i.e. in the cycloalkyl part of this group, is 1, 2, 3 or 4, in another embodiment 1, 2 or 3, in another embodiment 1 or 2, in another embodiment 1. In one embodiment, the number of substituents R47 which are optionally present on a phenyl-C(O)— group representing R40, i.e. in the phenyl part of this group, is 1, 2, 3 or 4, in another embodiment 1, 2 or 3, in another embodiment 1 or 2, in another embodiment 1.

In one embodiment of the invention, R40 is selected from the series consisting of $(C_1-C_4)$-alkyl which is optionally substituted by one or more identical or different substituents R41, phenyl which is optionally substituted by one or more identical or different substituents R43, Het1 which is optionally substituted by one or more identical or different substituents R44, $(C_1-C_4)$-alkyl-C(O)— which is optionally substituted by one or more identical or different substituents R45, $(C_3-C_7)$-cycloalkyl-C(O)— which is optionally substituted by one or more identical or different substituents R46, phenyl-C(O)— which is optionally substituted by one or more identical or different substituents R47, Het3-C(O)— which is optionally substituted by one or more identical or different substituents R48 and wherein Het3 is bonded via a ring carbon atom, R49-N(R50)-C(O)—, $(C_1-C_4)$-alkyl-S(O)$_2$— and R51-N(R52)-S(O)$_2$—. In another embodiment, R40 is selected from the series consisting of $(C_1-C_4)$-alkyl which is optionally substituted by one or more identical or different substituents R41, $(C_3-C_7)$-cycloalkyl which is optionally substituted by one or more identical or different substituents R42, phenyl which is optionally substituted by one or more identical or different substituents R43, and Het1 which is optionally substituted by one or more identical or different substituents R44, in another embodiment from the series consisting of $(C_1-C_4)$-alkyl which is optionally substituted by one or more identical or different substituents R41, phenyl which is optionally substituted by one or more identical or different substituents R43, and Het1 which is optionally substituted by one or more identical or different substituents R44. In another embodiment, R40 is selected from the series consisting of $(C_1-C_4)$-alkyl-C(O)— which is optionally substituted by one or more identical or different substituents R45, $(C_3-C_7)$-cycloalkyl-C(O)— which is optionally substituted by one or more identical or different substituents R46, phenyl-C(O)— which is optionally substituted by one or more identical or different substituents R47, Het3-C(O)— which is optionally substituted by one or more identical or different substituents R48 and wherein Het3 is bonded via a ring carbon atom, R49-N(R50)-C(O)—, $(C_1-C_4)$-alkyl-S(O)$_2$— and R51-N(R52)-S(O)$_2$—. In another embodiment, R40 is selected from the series consisting of $(C_1-C_4)$-alkyl-C(O)— which is optionally substituted by one or more identical or different substituents R45, $(C_3-C_7)$-cycloalkyl-C(O)— which is optionally substituted by one or more identical or different substituents R46, phenyl-C(O)— which is optionally substituted by one or more identical or different substituents R47, Het3-C(O)— which is optionally substituted by one or more identical or different substituents R48 and wherein Het3 is bonded via a ring carbon atom, and R49-N(R50)-C(O)—, in another embodiment from the series consisting of $(C_1-C_4)$-alkyl-C(O)— which is optionally substituted by one or more identical or different substituents R45, $(C_3-C_7)$-cycloalkyl-C(O)— which is optionally substituted by one or more identical or different substituents R46, phenyl-C(O)— which is optionally substituted by one or more identical or different substituents R47 and Het3-C(O)— which is optionally substituted by one or more identical or different substituents R48 and wherein Het3 is bonded via a ring carbon atom. In another embodiment, R40 is $(C_1-C_4)$-alkyl-C(O)— which is optionally substituted by one or more identical or different substituents R45. In another embodiment, R40 is $(C_3-C_7)$-cycloalkyl-C(O)— which is optionally substituted by one or more identical or different substituents R46. In another embodiment, R40 is phenyl-C(O)— which is optionally substituted by one or more identical or different substituents R47. In another embodiment, R40 is Het3-C(O)— which is optionally substituted by one or more identical or different substituents R48 and wherein Het3 is bonded via a ring carbon atom. In another embodiment, R40 is R49-N(R50)-C(O)—. In another embodiment, R40 is selected from the series consisting of $(C_1-C_4)$-alkyl-S(O)$_2$— and R51-N(R52)-S(O)$_2$—, in another embodiment R40 is $(C_1-C_4)$-alkyl-S(O)$_2$—, and in another embodiment R40 is R51-N(R52)-S(O)$_2$—.

In one embodiment of the invention, R41 is selected from the series consisting of $(C_3-C_7)$-cycloalkyl, $(C_1-C_4)$-alkyl-O—, R60-N(R61)-, R62-O—C(O)— and R63-N(R64)-C(O)—, in another embodiment from the series consisting of $(C_1-C_4)$-alkyl-O—, R60-N(R61)-, R62-O—C(O)— and R63-N(R64)-C(O)—, in another embodiment from the series consisting of R60-N(R61)-, R62-O—C(O)— and R63-N(R64)-C(O)—, in another embodiment from the series consisting of R60-N(R61)- and R62-O—C(O)—, and in another embodiment R41 is R60-N(R61)-.

In one embodiment of the invention, R42 is hydroxy, in another embodiment R42 is R65-N(R66)-.

In one embodiment of the invention, R43 is selected from the series consisting of halogen, $(C_1-C_4)$-alkyl, $(C_1-C_4)$-alkyl-O—, cyano, R67-O—C(O)— and R68-N(R69)-C(O)—, in another embodiment from the series consisting of halogen, $(C_1-C_4)$-alkyl, cyano, R67-O—C(O)— and R68-N(R69)-C(O)—, in another embodiment from the series consisting of halogen, $(C_1-C_4)$-alkyl, cyano and R67-O—C(O)—, in another embodiment from the series consisting of cyano and R67-O—C(O)—.

The group Het4, which can occur as a substituent R44 on a group Het1 representing R40, can be 4-membered, 5-membered, 6-membered or 7-membered. In one embodiment, Het4 is 4-membered to 6-membered, in another embodiment 5-membered to 6-membered, in another embodiment 5-membered, in another embodiment 6-membered. In one embodiment, Het4 comprises 1 further ring heteroatom in addition to the ring nitrogen atom via which Het4 is bonded, in another embodiment Het4 comprises 0 (zero) further ring heteroatom. In one embodiment, a further ring heteroatom in Het4 is selected from the series consisting of oxygen and sulfur, in another embodiment it is an oxygen atom, and in another embodiment it is a nitrogen atom. In one embodiment, the number of substituents R74 which are optionally present on Het4, is 1, 2, 3 or 4, in another embodiment it is 1, 2 or 3, in another embodiment it is 1 or 2, in another embodiment it is 1.

In one embodiment of the invention, R44 is selected from the series consisting of halogen, $(C_1-C_4)$-alkyl, hydroxy, oxo, R70-N(R71)-, $(C_1-C_4)$-alkyl-C(O)—N(R72)-, $(C_1-C_4)$-alkyl-S(O)$_2$—N(R73)- and Het4, in another embodiment from the series consisting of halogen, $(C_1-C_4)$-alkyl, hydroxy, oxo and $(C_1-C_4)$-alkyl-S(O)$_2$—N(R73)- and Het4, in another embodiment from the series consisting of halogen, $(C_1-C_4)$-alkyl, oxo and $(C_1-C_4)$-alkyl-S(O)$_2$—N(R73)- and Het4, in another embodiment from the series consisting of halogen, $(C_1-C_4)$-alkyl and oxo, wherein in all these embodiments Het4 is optionally substituted by one or more identical or different substituents R74. In one embodiment, the number of substituents Het4 representing R44 which is optionally present on a group Het1 representing R40, is 1 or 2, in another embodiment it is 1.

In one embodiment of the invention, R45 is selected from the series consisting of cyano, $(C_1-C_4)$-alkyl-O—, phenyl-O—, phenyl-$(C_1-C_4)$-alkyl-O—, oxo, R75-N(R76)- and R77-C(O)—N(R78)-, in another embodiment from the series consisting of cyano, $(C_1-C_4)$-alkyl-O—, phenyl-O—, oxo, R75-N(R76)- and R77-C(O)—N(R78)-, in another embodiment from the series consisting of cyano, $(C_1-C_4)$-alkyl-O—, phenyl-O—, R75-N(R76)- and R77-C(O)—N(R78)-, in another embodiment from the series consisting of $(C_1-C_4)$-alkyl-O—, phenyl-O—, R75-N(R76)- and R77-C(O)—N(R78)-, in another embodiment from the series consisting of phenyl-O—, R75-N(R76)- and R77-C(O)—N(R78)-, in another embodiment from the series consisting of R75-N(R76)- and R77-C(O)—N(R78)-, and in another embodiment R45 is R75-N(R76)-.

In one embodiment of the invention, R46 is hydroxy, in another embodiment R46 is R79-N(R80)-.

In one embodiment of the invention, R47 is selected from the series consisting of halogen, $(C_1-C_4)$-alkyl and $(C_1-C_4)$-alkyl-O—, in another embodiment R47 is $(C_1-C_4)$-alkyl-O—.

In one embodiment of the invention, R48 is selected from the series consisting of halogen, $(C_1-C_4)$-alkyl, hydroxy and oxo, in another embodiment from the series consisting of halogen, $(C_1-C_4)$-alkyl and $(C_1-C_4)$-alkyl-O—, in another embodiment from the series consisting of hydroxy and oxo, where an oxo group or an hydroxy group can also be present on a suitable ring nitrogen atom of the group Het3 on which R48 is an optional substituent, such as on the ring nitrogen atom of a pyridine ring or the ring nitrogen atom of pyridine moiety of a isothiazolo[5,4-b]pyridine ring representing a group Het3 occurring in R40, to give the respective N-oxide, as already outlined above. Suitable nitrogen heterocycles representing a group Het3 occurring in R40 are thus are also comprised in the form of the N-oxides.

In one embodiment of the invention, R49 and R51 are independently of one another selected from the series consisting of hydrogen, $(C_1-C_4)$-alkyl, $(C_3-C_7)$-cycloalkyl and $(C_3-C_7)$-cycloalkyl-$(C_1-C_4)$-alkyl-, in another embodiment from the series consisting of hydrogen, $(C_1-C_4)$-alkyl and $(C_3-C_7)$-cycloalkyl, in another embodiment from the series consisting of hydrogen and $(C_1-C_4)$-alkyl, and in another embodiment they are hydrogen.

In one embodiment of the invention, R50 and R52 are independently of one another selected from the series consisting of hydrogen, $(C_1-C_4)$-alkyl and $(C_3-C_7)$-cycloalkyl, in another embodiment from the series consisting of hydrogen and $(C_1-C_4)$-alkyl, and in another embodiment they are hydrogen.

In one embodiment of the invention, R60, R61, R62, R63, R64, R65, R66, R67, R68, R69, R70, R71, R72, R73, R76, R78, R79, R80, R81, R82, R83 and R84 are independently of one another selected from the series consisting of hydrogen and $(C_1-C_2)$-alkyl, and in another embodiment they are hydrogen.

In one embodiment of the invention, R74 is $(C_1-C_4)$-alkyl.

In one embodiment of the invention, R75 is selected from the series consisting of hydrogen, $(C_1-C_4)$-alkyl, $(C_3-C_7)$-cycloalkyl and $(C_3-C_7)$-cycloalkyl-$(C_1-C_4)$-alkyl-, in another embodiment from the series consisting of hydrogen, $(C_1-C_4)$-alkyl and $(C_3-C_7)$-cycloalkyl, in another embodiment from the series consisting of hydrogen and $(C_1-C_4)$-alkyl, in another embodiment they are hydrogen, and in another embodiment they are $(C_1-C_4)$-alkyl.

In one embodiment of the invention, R77 is $(C_1-C_4)$-alkyl, and in another embodiment R77 is R83-N(R84)-$(C_1-C_4)$-alkyl-.

A subject of the invention are all compounds of the formula I wherein any one or more structural elements such as groups, residues, substituents and numbers are defined as in any of the specified embodiments or definitions of the elements, or have one or more of the specific meanings which are mentioned herein as examples of elements, wherein all combinations of one or more definitions of compounds or elements and/or specified embodiments and/or specific meanings of elements are a subject of the present invention. Also with respect to all such compounds of the formula I, all their stereoisomeric forms and mixtures of stereoisomeric forms in any ratio, and their pharmaceutically acceptable salts are a subject of the present invention.

As an example of compounds of the invention which with respect to any structural elements are defined as in specified embodiments of the invention or definitions of such elements, compounds of the formula I may be mentioned wherein X is =N(O)—;
R1, R2 and R3 are independently of one another selected from the series consisting of hydrogen, halogen, $(C_1-C_4)$-alkyl and cyano;
R10 is selected from the series consisting of $(C_1-C_4)$-alkyl, $(C_3-C_7)$-cycloalkyl, $(C_3-C_7)$-cycloalkyl-$(C_1-C_4)$-alkyl- and $(C_1-C_4)$-alkyl-O—$(C_1-C_4)$-alkyl-;
in any of their stereoisomeric forms or a mixture of stereoisomeric forms in any ratio, and the pharmaceutically acceptable salt thereof.

As another such example, compounds of the formula I may be mentioned, wherein
X is selected from the series consisting of =N— and =N(O)—;
R1, R2 and R3 are independently of one another selected from the series consisting of hydrogen, halogen, $(C_1-C_4)$-alkyl, cyano, $(C_1-C_4)$-alkyl-O—C(O)— and R4-N(R5)-C(O)—;
R4 is selected from the series consisting of hydrogen, $(C_1-C_4)$-alkyl, $(C_3-C_7)$-cycloalkyl and $(C_3-C_7)$-cycloalkyl-$(C_1-C_4)$-alkyl-;
R5 is selected from the series consisting of hydrogen and $(C_1-C_4)$-alkyl;
R10 is selected from the series consisting of hydrogen, $(C_1-C_4)$-alkyl, $(C_3-C_7)$-cycloalkyl, $(C_3-C_7)$-cycloalkyl-$(C_1-C_4)$-alkyl- and $(C_1-C_4)$-alkyl-O—$(C_1-C_4)$-alkyl-, with the proviso that R10 can only be hydrogen if X is =N(O)—;
R11 is selected from the series consisting of $(C_1-C_4)$-alkyl which is optionally substituted by one or more identical or different substituents R12, $(C_3-C_7)$-cycloalkyl which is optionally substituted by one or more identical or different substituents R13, and Het2 which is optionally substituted by one or more identical or different substituents R14 and wherein Het2 is bonded via a ring carbon atom;
or the groups R10 and R11, together with the nitrogen atom carrying them, form a 4-membered to 10-membered, monocyclic or bicyclic, saturated or partially unsaturated heterocycle which, in addition to the nitrogen atom carrying R10 and R11, comprises 0 or 1 further ring heteroatoms selected from the series consisting of nitrogen, oxygen and sulfur, which is optionally substituted on ring carbon atoms by one or more identical or different substituents R30, and which is optionally substituted on further ring nitrogen atoms by one or more identical or different substituents R40;
R12 is selected from the series consisting of phenyl, Het3, hydroxy, $(C_1-C_4)$-alkyl-O—, R15-N(R16)- and R17-C(O)—N(R18)-, wherein phenyl and Het3 independently of one another are optionally substituted by one or more identical or different substituents R19;
R13 is selected from the series consisting of hydroxy, $(C_1-C_4)$-alkyl-O— and cyano;
R14 is selected from the series consisting of $(C_1-C_4)$-alkyl, hydroxy, $(C_1-C_4)$-alkyl-C(O)—O—, HO—$(C_1-C_4)$-alkyl-, $(C_1-C_4)$-alkyl-C(O)—O—$(C_1-C_4)$-alkyl- and $(C_1-C_4)$-alkyl-C(O)—;
R15, R16 and R18 are independently of one another selected from the series consisting of hydrogen and $(C_1-C_4)$-alkyl;
R17 is selected from the series consisting of $(C_1-C_4)$-alkyl, $(C_3-C_7)$-cycloalkyl and $(C_3-C_7)$-cycloalkyl-$(C_1-C_4)$-alkyl-;
R19 is selected from the series consisting of halogen, $(C_1-C_4)$-alkyl, hydroxy, $(C_1-C_4)$-alkyl-O—, $(C_1-C_4)$-alkyl-C(O)—O—;
R30 is selected from the series consisting of fluorine, $(C_1-C_4)$-alkyl, Het2, hydroxy, oxo, $(C_1-C_4)$-alkyl-O—, R31-N(R32)-, $(C_1-C_4)$-alkyl-C(O)—, R33-O—C(O)— and R34-N(R35)-C(O)—, wherein Het2 is optionally substituted by one or more identical or different substituents R36;
R31, R32, R33, R34 and R35 are independently of one another selected from the series consisting of hydrogen and $(C_1-C_4)$-alkyl;
R36 is selected from the series consisting of fluorine, $(C_1-C_4)$-alkyl, hydroxy and oxo;
R40 is selected from the series consisting of $(C_1-C_4)$-alkyl which is optionally substituted by one or more identical or different substituents R41, $(C_3-C_7)$-cycloalkyl which is optionally substituted by one or more identical or different substituents R42, phenyl which is optionally substituted by one or more identical or different substituents R43, Het1 which is optionally substituted by one or more identical or different substituents R44, $(C_1-C_4)$-alkyl-C(O)— which is optionally substituted by one or more identical or different substituents R45, $(C_3-C_7)$-cycloalkyl-C(O)— which is optionally substituted by one or more identical or different substituents R46, phenyl-C(O)— which is optionally substituted by one or more identical or different substituents R47, Het3-C(O)— which is optionally substituted by one or more identical or different substituents R48 and wherein Het3 is bonded via a ring carbon atom, R49-N(R50)-C(O)—, ($C_1$-$C_4$)-alkyl-S(O)$_2$— and R51-N(R52)-S(O)$_2$—;

R41 is selected from the series consisting of ($C_1$-$C_4$)-alkyl-O—, R60-N(R61)-, R62-O—C(O)— and R63-N(R64)-C(O)—;

R42 is selected from the series consisting of R65-N(R66)-;

R43 is selected from the series consisting of halogen, ($C_1$-$C_4$)-alkyl, ($C_1$-$C_4$)-alkyl-O—, cyano, R67-O—C(O)— and R68-N(R69)-C(O)—;

R44 is selected from the series consisting of halogen, ($C_1$-$C_4$)-alkyl, hydroxy, oxo, ($C_1$-$C_4$)-alkyl-S(O)$_2$—N(R73)- and Het4, wherein Het4 is optionally substituted by one or more identical or different substituents R74;

R45 is selected from the series consisting of cyano, ($C_1$-$C_4$)-alkyl-O—, phenyl-O—, phenyl-($C_1$-$C_4$)-alkyl-O—, oxo, R75-N(R76)- and R77-C(O)—N(R78)-;

R46 is selected from the series consisting of R79-N(R80)-;

R47 is selected from the series consisting of halogen, ($C_1$-$C_4$)-alkyl, ($C_1$-$C_4$)-alkyl-O— and R81-N(R82)-C(O)—;

R48 is selected from the series consisting of halogen, ($C_1$-$C_4$)-alkyl, hydroxy and oxo;

R49 and R51 are independently of one another selected from the series consisting of hydrogen, ($C_1$-$C_4$)-alkyl, ($C_3$-$C_7$)-cycloalkyl and ($C_3$-$C_7$)-cycloalkyl-($C_1$-$C_4$)-alkyl-;

R50 and R52 are independently of one another selected from the series consisting of hydrogen and ($C_1$-$C_4$)-alkyl;

R60, R61, R62, R63, R64, R65, R66, R67, R68, R69, R73, R76, R78, R79, R80, R81, R82, R83 and R84 are independently of one another selected from the series consisting of hydrogen and ($C_1$-$C_4$)-alkyl;

R74 is selected from the series consisting of fluorine and ($C_1$-$C_4$)-alkyl;

R75 is selected from the series consisting of hydrogen, ($C_1$-$C_4$)-alkyl, ($C_3$-$C_7$)-cycloalkyl and ($C_3$-$C_7$)-cycloalkyl-($C_1$-$C_4$)-alkyl-;

R77 is selected from the series consisting of ($C_1$-$C_4$)-alkyl and R83-N(R84)-($C_1$-$C_4$)-alkyl-;

Het1 is a monocyclic, 4-membered to 7-membered, saturated, partially unsaturated or aromatic heterocycle which comprises 1, 2 or 3 identical or different ring heteroatoms selected from the series consisting of nitrogen oxygen and sulfur, and which is bonded via a ring carbon atom;

Het2 is a monocyclic, 4-membered to 7-membered, saturated heterocycle which comprises 1 or 2 identical or different ring heteroatoms selected from the series consisting of nitrogen, oxygen and sulfur;

Het3 is a monocyclic or bicyclic, 4-membered to 12-membered, saturated, partially unsaturated or aromatic heterocycle which comprises 1, 2 or 3 identical or different ring heteroatoms selected from the series consisting of nitrogen, oxygen and sulfur;

Het4 is a monocyclic, 4-membered to 7-membered, saturated heterocycle which comprises a ring nitrogen atom via which Het4 is bonded, and 0 or 1 further ring heteroatom selected from the series consisting of nitrogen, oxygen and sulfur;

wherein all phenyl groups are optionally substituted by one or more identical or different substituents selected from the series consisting of halogen, ($C_1$-$C_4$)-alkyl, cyano, hydroxy and ($C_1$-$C_4$)-alkyl-O—, unless specified otherwise;

wherein all cycloalkyl groups, independently of any other substituents which can be present on a cycloalkyl group, are optionally substituted by one or more identical or different substituents selected from the series consisting of fluorine and ($C_1$-$C_4$)-alkyl;

wherein all alkyl groups, independently of any other substituents which can be present on an alkyl group, are optionally substituted by one or more fluorine substituents;

in any of their stereoisomeric forms or a mixture of stereoisomeric forms in any ratio, and the pharmaceutically acceptable salt thereof.

A subject of the invention also is a compound of the formula I which is selected from any of the specific compounds of the formula I which are disclosed herein, or is any one of the specific compounds of the formula I which are disclosed herein, irrespective thereof whether they are disclosed as a free compound and/or as a specific salt, or a pharmaceutically acceptable salt thereof, wherein the compound of the formula I is a subject of the invention in any of its stereoisomeric forms or a mixture of stereoisomeric forms in any ratio, unless a specific stereoisomeric form is specified with respect to any carbon atoms in the respective compound.

Another subject of the present invention are processes for the preparation of the compounds of the formula I which are outlined below and by which the compounds of the formula I and intermediates occurring in the course of their synthesis are obtainable. For example, one such process comprises the reaction of a isothiazolo[5,4-b]pyridin-3 one of the formula II with a carbamoyl chloride of the formula III to give a compound of the formula I in which X is =N—, i.e. a compound of the formula Ia, which can then be oxidized to give a compound of the formula I in which X is =N(O)—, i.e. the N-oxide of the formula Ib.

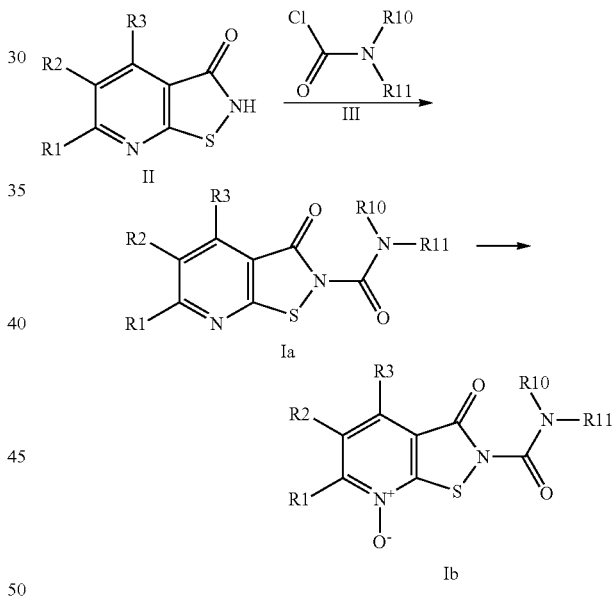

The groups R1, R2, R3, R10 and R11 in the compounds of the formulae II and III and the initially obtained compounds of the formulae Ia and Ib are defined as in the compounds of the formula I, and additionally can functional groups can be present in protected form or in the form of precursor groups which are subsequently converted into the groups present in the final compound of the formula Ia or Ib. In case a compound is to be prepared in which R10 is hydrogen, instead of the carbamoyl chloride of the formula III, the respective isocyanate of the formula O=C=N—R11 may be employed in the reaction. The reaction of the compounds of the formulae II and III is usually performed in an inert organic solvent, for example a hydrocarbon like toluene, a chlorinated hydrocarbon like dichloromethane, a nitrile like acetonitrile or an amide like dimethylformamide, or a mixture of solvents, at temperatures from about 20° C. to about 100° C., for example at temperatures from about 40° C. to about 80° C., such as at about 60° C., in the presence of a suitable base such as a tertiary amine like triethylamine, diisopropylethylamine or N-methylmorpholine. The conversion of a compound of the formula Ia into the N-oxide of the formula Ib can be performed under standard conditions for the preparation of N-oxides of aromatic nitrogen heterocycles, for example by treatment with hydrogen peroxide or a peracid or a salt thereof, favorably by treatment with commercially available potassium peroxomonosulfate (Oxone®) in a solvent such as water or an alcohol like methanol or ethanol or a mixture thereof at about room temperature, i.e. at about 20° C. to about 25° C.

Compounds of the formula Ib can further be obtained by treating a compound of the formula Ib, which has been obtained as outlined before and which is smoothly available, for example a compound of the formula Ib in which R10 and R11 together with the nitrogen atom carrying them form a morpholine ring, with a base to give a compound of the formula IV, which is then converted into another compound of the formula Ib by reaction with a carbamoyl chloride of the formula III or with an amine of the formula V and phosgene or a phosgene equivalent.

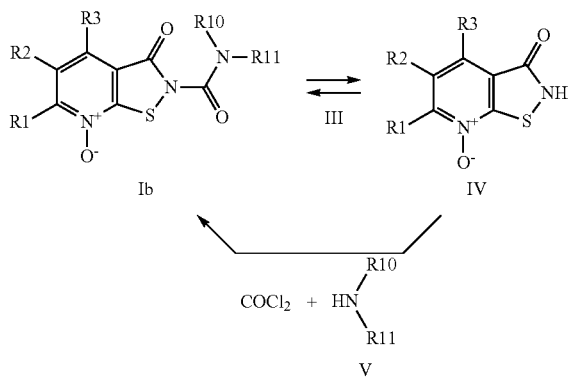

The groups R1, R2, R3, R10 and R11 in the compounds of the formulae IV and V and the compound of the formula Ib which is initially obtained according to this process, are defined as in the compounds of the formula I, and additionally functional groups can be present in protected form or in the form of precursor groups which are subsequently converted into the groups present in the final compound of the formula Ib. For preparing a compound of the formula IV, a compound of the formula Ib can be treated with a base, for example an alkaline metal hydroxide like sodium hydroxide, in an inert solvent, for example an organic solvent such as a nitrile like acetonitrile or water or a mixture thereof, at about room temperature. The conversion of the compound of the formula IV into another compound of the formula Ib can be performed by reaction with a carbamoyl chloride similarly as outlined above with respect to reaction of the compounds of the formulae II and III. Instead of a carbamoyl chloride of the formula III, in such conversion also an amine of the formula V and phosgene or a phosgene equivalent can be employed which form in situ a carbamoyl chloride or, in case R10 is hydrogen, an isocyanate, which is subsequently reacted with the compound of the formula IV. The reaction of the amine of the formula V and phosgene or a phosgene equivalent and the subsequent reaction with the compound of the formula IV can be performed under similar conditions as outlined above with respect to reaction of the compounds of the formulae II and III, for example in an inert organic solvent such as a hydrocarbon like toluene, a chlorinated hydrocarbon like dichloromethane or a nitrile like acetonitrile, or a mixture of solvents, at temperatures from about 20° C. to about 100° C., for example at temperatures from about 20° C. to about 40° C., in the presence of a suitable base such as a tertiary amine like triethylamine, diisopropylethylamine or N-methylmorpholine, wherein the detailed conditions depend on the particulars of the specific case and, as usual, are readily chosen by a person skilled in the art.

For obtaining further compounds of the formula I, various transformations of functional groups can be carried out under standard conditions in compounds of the formula I obtained as described above, or in intermediates or starting compounds in the synthesis of the compounds of the formula I. For example, a hydroxy group or an amino group, including ring nitrogen atoms in heterocycles which can be acylated, can be reacted with a carboxylic acid, for example in the presence of an activating agent such as thionyl chloride or oxalyl chloride which lead to the formation of the acid chloride, or in the presence of a coupling agent such an N,N'-carbonyldiazole like N,N'-carbonyldiimidazole (CU), a carbodiimide like 1,3-diisopropylcarbodiimide (DIC), 1,3-dicyclohexylcarbodiimide (DCC) or 1-(3-dimethylaminopropyl)-3-ethylcarbodiimide hydrochloride (EDC), or a uronium-based coupling reagents like O-(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU) or O-(cyano(ethoxycarbonyl)methyleneamino)-N,N,N',N'-tetramethyluronium tetrafluoroborate (TOTU), for example, in an inert solvent, for example a hydrocarbon like toluene, a chlorinated hydrocarbon like dichloromethane, an ether like tetrahydrofuran, dioxane or 1,2-dimethoxyethane, or an amide like dimethylformamide or N-methylpyrrolidin-2-one, generally in the presence of a base such as a tertiary amine like triethylamine, diisopropylethylamine, N-methylmorpholine or pyridine, or an inorganic base. Similarly, amino groups can be sulfonylated by reaction with sulfonic acids or activated derivatives thereof such as sulfonic acid chlorides. Etherifications of hydroxy groups can be performed by alkylation with the respective halogen compound, for example a bromide or iodide, in the presence of a base such an alkali metal carbonate like potassium carbonate or cesium carbonate in an inert solvent such as an amide like dimethylformamide or N-methylpyrrolidin-2-one or a ketone like acetone or butan-2-one, or with the respective alcohol under the conditions of the Mitsunobu reaction in the presence of a phosphine like triphenylphosphine or tributylphosphine and an azodicarboxylic acid derivative like diethyl azodicarboxylate or diisopropyl azodicarboxylate. By treatment with a suitable halogenating agent, a hydroxy group can be converted into a halide. A halogen atom can be replaced with a variety of groups in a substitution reaction which may also be a transition-metal catalyzed reaction. An amino group can be modified under standard conditions for alkylation, for example by reaction with a halogen compound or by reductive amination of a carbonyl compound. By reaction with a carbamoyl chloride or an isocyanate, an amino group can be converted into a urea derivative. A carboxylic acid ester group can be hydrolyzed under acidic or basic conditions to give a carboxylic acid. A carboxylic acid group can be activated or converted into a reactive derivative as outlined above and reacted with an alcohol or an amine or ammonia to give an ester or amide. A primary amide group $H_2N-C(O)-$ can be dehydrated to give a nitrile group (cyano group, NC—). A sulfur atom can be oxidized with a peroxide like hydrogen peroxide or a peracid to give a sulfoxide moiety (S(O)) or a sulfone moiety (S(O)$_2$). A carboxylic acid group, carboxylic acid ester group and a ketone group can be reduced to an alcohol, for example with a complex hydride such al lithium aluminum hydride, lithium borohydride or sodium borohydride. A hydroxy group can be oxidized to an oxo group by means of pyridinium chlorochromate or the Dess-Martin periodinane reagent, for example. All such reactions in the preparation of the compounds of the formula I are known per se and can be carried out in a manner familiar to a person skilled in the art according to, or analogously, to procedures which are described in the standard literature, for example in Houben-Weyl, Methods of Organic Chemistry, Thieme; or Organic Reactions, John Wiley & Sons; or R. C. Larock, Comprehensive Organic Transformations: A Guide to Functional Group Preparations, 2. ed. (1999), John Wiley & Sons, and the references quoted therein.

As already indicated, it can be advantageous or necessary in all reactions which are carried out in the course of the preparation of the compounds of the formula I to temporarily protect functional groups or have them initially present in the form of precursor groups, and later deprotect them or convert them into the desired groups. Appropriate synthesis strategies and protective groups and precursor groups which are suitable for the respective case, are known to the person skilled in the art and can be found in P. G. M. Wuts and T. W. Greene, Greene's Protective Groups in Organic Synthesis, 4. ed. (2007), John Wiley & Sons, for example. Examples of protective groups which may be mentioned, are benzyl protective groups, for example benzyl ethers of hydroxy compounds and benzyl esters of carboxylic acids, from which the benzyl group can be removed by catalytic hydrogenation in the presence of a palladium catalyst, tert-butyl protective groups, for example tert-butyl esters of carboxylic acids, from which the tert-butyl group can be removed by treatment with trifluoroacetic acid, acyl protective groups, for example ester and amides of hydroxy compounds and amino compounds, which can be cleaved again by acidic or basic hydrolysis, alkoxycarbonyl protective groups, for example tert-butoxycarbonyl derivatives of amino compounds, which can be cleaved again by treatment with trifluoroacetic acid, or benzyloxycarbonyl derivatives of amino compounds, which can be cleaved by catalytic hydrogenation in the presence of palladium catalyst. Examples of precursors which may be mentioned are halogen atoms which can be replaced by many other groups, or nitro groups which can be converted, for example by catalytic hydrogenation, into amino groups which can be diazotized and converted into a large number of groups.

As is usual and applies to all reactions performed in the course of the synthesis of a compound of the formula I, appropriate details of the conditions applied in a specific preparation process, including the solvent, a base or acid, the temperature, the order of addition, the molar ratios and other parameters, are routinely chosen by the skilled person in view of the characteristics of the starting compounds and the target compound and the other particularities of the specific case. As is also known by the skilled person, not all processes described herein will in the same way be suitable for the preparation of all compounds of the formula I and their intermediates, and adaptations have to be made. In all processes for the preparation of the compounds of the formula I, workup of the reaction mixture and the purification of the product is performed according to customary methods known to the skilled person which include, for example, quenching of a reaction mixture with water, adjustment of a certain pH, precipitation, extraction, drying, concentration, crystallization, distillation and chromatography. Also for the characterization of the product, customary methods are used such as NMR, IR and mass spectroscopy.

The starting materials employed in the processes outlined above are commercially available or can be prepared according to procedures, or in analogy to procedures, described in the literature. As already outlined above, carbamoyl chlorides of the formula III and isocyanates in case R10 is hydrogen, can readily be obtained from the respective amines of the formula V, which are commercially available or can be prepared according to literature procedures with great structural diversity, by reaction with phosgene or a phosgene equivalent. Isothiazolo[5,4-b]pyridin-3-ones of the formula II can be prepared, for example, from 2-mercaptonicotinic acids of the formula VI, which can be obtained from the respective 2-chloronicotinic acids with thiourea, for example, or their acid amides of the formula VII according to procedures described in the literature.

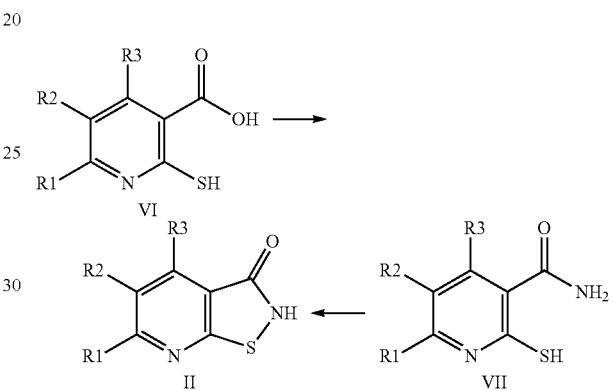

The groups R1, R2 and R3 in the compounds of the formulae VI and VII are defined as in the compounds of the formula I, and additionally functional groups can be present in protected form or in the form of precursor groups which are subsequently converted into the groups present in the final compound of the formula I. For example, compounds of the formula VI can be reacted with diphenylphosphoryl azide in pyridine in the presence of a tertiary amine like triethylamine at temperatures from about 0° C. to about 20° C. to give compounds of the formula II, according to the procedure described by Chiyoda, T. et al., Synlett 2000: 1427-1428. Compounds of the formula VII, which can be obtained starting from compounds of the formula VI, can be oxidatively cyclized to compounds of the formula II by treatment with concentrated sulfuric acid at temperatures of about 100° C., according to the procedure described by Wright, S. W. et al., Org. Prep. Proced. Int. 1993, 25: 247-249, and Furkas, S. D. et al., Bioorg. Med. Chem. 2011, 19: 3678-3689.

Another subject of the present invention are the novel starting compounds and intermediates occurring in the synthesis of the compounds of the formula I, including the compounds of the formulae II, III, IV, V, VI and VII, wherein the groups R1, R2, R3, R10 and R11 are defined as above, in any of their stereoisomeric forms or a mixture of stereoisomeric forms in any ratio, and their salts, and their use as synthetic intermediates or starting compounds. All general explanations, specifications of embodiments and definitions of numbers and groups given above with respect to the compounds of the formula I apply correspondingly to the said intermediates and starting compounds.

The compounds of the formula I inhibit transglutaminases, especially transglutaminase 2 (TGM2), as can be shown in the pharmacological test described below and in other pharmacological tests which are known to a person skilled in the art, including animal models in which the effect of the compounds can be determined ex vivo or in vivo. The compounds of the formula I and their pharmaceutically acceptable salts therefore are valuable pharmaceutical active compounds. The compounds of the formula I and their pharmaceutically active salts can in particular be used for the treatment of joint diseases, degenerative joint diseases, osteoarthritis, degenerative intervertebral disk diseases, degenerative disk diseases, neurodegenerative diseases, Alzheimer's disease, Parkinson's disease, Huntington's disease, amyotrophic lateral sclerosis, cerebellar ataxis, cancer, glioblastomas, malignant melanomas, pancreatic ductal carcinomas, adenocarcinomas, celiac disease, fibrosis or liver cirrhosis, for example. The treatment of diseases is to be understood as meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals which are susceptible thereto and are in need of such a prophylaxis or prevention, with the aim of a prevention or suppression of their occurrence or of an attenuation in the case of their occurrence. The treatment of diseases can occur both in acute cases and in chronic cases. The compounds of the formula I and their pharmaceutically acceptable salts can in general be used in disorders in which an inhibition of transglutaminases, in particular TGM2, is intended by the physician for improving the patient's condition, where the compounds of the formula I and their pharmaceutically acceptable salts can also be employed in cases where only a certain partial inhibition of transglutaminase activity is intended, for example by use of a low dosage.

The compounds of the formula I and their pharmaceutically acceptable salts can therefore be used in animals, in particular in mammals and specifically in humans, as a pharmaceutical or medicament on their own, in mixtures with one another, or in the form of pharmaceutical compositions. A subject of the present invention also are the compounds of the formula I and their pharmaceutically acceptable salts for use as a pharmaceutical. A subject of the present invention also are pharmaceutical compositions and medicaments which comprise at least one compound of the formula I and/or a pharmaceutically acceptable salt thereof as an active ingredient, in an effective dose for the desired use, and a pharmaceutically acceptable carrier, i.e. one or more pharmaceutically innocuous, or nonhazardous, vehicles and/or excipients, and optionally one or more other pharmaceutical active compounds. A subject of the present invention also are the compounds of the formula I and their pharmaceutically acceptable salts for use in the treatment of the diseases mentioned above or below, including the treatment of any one of the mentioned diseases, for example degenerative joint diseases, degenerative intervertebral disk diseases, osteoarthritis, neurodegenerative diseases, cancer, celiac disease, fibrosis or liver cirrhosis, wherein treatment of diseases comprises their therapy and prophylaxis as mentioned above, or for use an inhibitor of transglutaminases, in particular TGM2. A subject of the present invention also are the use of the compounds of the formula I and their pharmaceutically acceptable salts for the manufacture of a medicament for the treatment of the diseases mentioned above or below, including the treatment of any one of the mentioned diseases, for example degenerative joint diseases, degenerative intervertebral disk diseases, osteoarthritis, neurodegenerative diseases, cancer, celiac disease, fibrosis or liver cirrhosis, wherein treatment of diseases comprises their therapy and prophylaxis as mentioned above, or a medicament for inhibition of transglutaminases, in particular TGM2. A subject of the present invention also are methods for the treatment of the diseases mentioned above or below, including the treatment of any one of the mentioned diseases, for example degenerative joint diseases, degenerative intervertebral disk diseases, osteoarthritis, neurodegenerative diseases, cancer, celiac disease, fibrosis or liver cirrhosis, wherein treatment of diseases comprises their therapy and prophylaxis as mentioned above, and a method for inhibiting transglutaminases, in particular TGM2, which comprise administering an efficacious amount of at least one compound of the formula I and/or a pharmaceutically acceptable salt thereof to a human or an animal which is in need thereof. The compounds of the formula I and their pharmaceutically acceptable salts, and pharmaceutical compositions and medicaments comprising them, can be administered enterally, for example by oral or rectal administration, parenterally, for example by intravenous, intramuscular, subcutaneous or intraarticular injection or infusion, or by another type of administration such as topical, percutaneous, transcutaneous or inhalative administration, the preferred form of administration depending on the particulars of the specific case. The compounds of the formula I and their pharmaceutically acceptable salts can also be used in combination with other pharmaceutical active compounds.

The pharmaceutical compositions and medicaments according to the invention normally contain from about 0.5 to about 90 percent by weight of a compound or compounds of the formula I or pharmaceutically acceptable salts thereof, and an amount of active ingredient of the formula I and/or its pharmaceutically acceptable salt which in general is from about 0.1 mg to about 1 g, in particular from about 0.2 mg to about 500 mg, for example from about 1 mg to about 300 mg, per dose unit. Depending on the kind of the pharmaceutical composition and other particulars of the specific case, the amount may deviate from the indicated ones. The production of the pharmaceutical compositions and medicaments can be carried out in a manner known per se and familiar to the person skilled in the art. For this, the compounds of the formula I and/or their pharmaceutically acceptable salts are mixed together with one or more solid or liquid vehicles and/or excipients, if desired also in combination with one or more other pharmaceutical active compounds, and brought into a suitable form for dosage and administration, which can then be used in human medicine or veterinary medicine.

As vehicles, which may also be looked upon as diluents or solvents or bulking agents, and excipients suitable organic and inorganic substances can be used which do not react in an undesired manner with the compounds of the formula I. As examples of types of excipients, or additives, which can be contained in the pharmaceutical compositions and medicaments, lubricants, preservatives, gel formers, thickeners, stabilizers, disintegrants, wetting agents, emulsifiers, dispersants, antifoaming agents, salts, buffer substances, colorants, flavorings and antioxidants may be mentioned. Examples of vehicles and excipients are water, physiological saline, vegetable oils such as sunflower oil, animal oils such as fish liver oil, waxes, alcohols such as ethanol, isopropanol, 1,2-propanediol, glycerol, polyols, polyethylene glycols, polyvinylpyrrolidone, gelatin, gum arabic, cellulose, carbohydrates such as glucose, lactose or starch like corn starch, magnesium carbonate, potassium phosphate, sodium chloride, stearic acid and its salts such as magnesium stearate, talc, lanolin, petroleum jelly, or mixtures thereof, for example mixtures of water or saline with one or more organic solvents such as mixtures of water with alcohols.

For oral and rectal use, pharmaceutical forms such as, for example, tablets, coated tablets, sugar-coated tablets, granules, hard and soft gelatin capsules, suppositories, solutions, including oily, alcoholic or aqueous solutions, or drops, furthermore suspensions or emulsions, can be used. For parenteral use, for example by injection or infusion, pharmaceutical forms such as solutions, for example aqueous solutions, can be used. For topical use, pharmaceutical forms such as ointments, creams, pastes, lotions, gels, sprays, foams, aerosols, solutions or powders can be used. Pharmaceutical formulations such as, for example, aerosols and sprays may comprise solutions, suspensions or emulsions of the active ingredient in a pharmaceutically acceptable solvent, such as ethanol or water, or a mixture of such solvents. The formulation may also comprise other pharmaceutical excipients such as surfactants, emulsifiers and stabilizers, and a propellant gas.

As usual, the dosage of the compounds of the formula I and the frequency of administration depend on the circumstances of the specific case and is adjusted by the physician according to the customary rules and procedures. It depends, for example, on the compound of the formula I administered and its potency and duration of action, on the nature and severity of the individual syndrome, on the gender, age, weight and the individual responsiveness of the human or animal to be treated, on whether the treatment is acute or chronic or prophylactic, or on whether further pharmaceutical active compounds are administered in addition to a compound of the formula I. Normally, in the case of administration to an adult weighing about 75 kg, a dose from about 0.1 mg to about 100 mg per kg per day, in particular from about 1 mg to about 10 mg per kg per day (in each case in mg per kg of body weight), is sufficient. The daily dose can be administered in the form of a single dose or divided into a number of individual doses, for example two, three or four individual doses. The administration can also be carried out continuously, for example by continuous injection or infusion. Depending on the individual behavior in a specific case, it may be necessary to deviate upward or downward from the indicated dosages.

Besides as a pharmaceutical active compound in human medicine and veterinary medicine, the compounds of the formula I can also be employed as an aid in biochemical investigations or as a scientific tool or for diagnostic purposes, for example in in vitro diagnoses of biological samples, if an inhibition of transglutaminases is intended. The compounds of the formula I and their salts can also be used as intermediates for the preparation of further pharmaceutical active substances.

The following examples illustrate the invention.

When example compounds containing a basic group were purified by preparative high performance liquid chromatography (HPLC) on reversed phase (RP) column material and, as customary, the eluent was a gradient mixture of water and acetonitrile containing trifluoroacetic acid, they were in part obtained in the form of their acid addition salts with trifluoroacetic acid, depending on the details of the workup such as evaporation or lyophilization conditions. In the names and structural formulae of the example compounds such contained trifluoroacetic acid is not specified.

The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. In the MS characterization, in general the mass number (m/z) of the peak of the molecular ion [M], for example [M$^+$], or of a related ion such as the ion [M+1], for example [(M+1)$^+$], i.e. the protonated molecular ion [(M+H)$^+$] ([MH$^+$]), or the ion [M−1], for example [(M−1)$^-$], i.e. the deprotonated molecular ion [(M−H)$^-$], which was formed depending on the ionization method used, is given. The particulars of the LC/MS methods used are as follows. "ACN" means acetonitrile, "TFA" means trifluoroacetic acid, and "FA" means formic acid. Unless specified otherwise, the MS ionization method was electrospray ionization ES+.

LC/MS Method A: Column: YMC Jsphere, 33×2 mm, 4 μm; eluent A: water+0.05% TFA; eluent B: ACN+0.05% TFA; gradient: 95 A: 5% B (0 min) to 5% A: 95% B (2.5 min) to 95% A: 5% B (3.2 min)

LC/MS Method B: Column: YMC Jsphere, 33×2 mm, 4 μm; eluent A: water+0.1% FA; eluent B: ACN+0.08% FA; gradient: 95% A: 5% B (0 min) to 5% A: 95% B (2.5 min)

LC/MS Method C: Column: Waters XBridge C18, 50×4.6 mm, 2.5 μm; eluent A: water+0.05% TFA; eluent B: ACN+0.05% TFA; gradient: 95% A: 5% B (0 min) to 95% A: 5% B (0.3 min) to 5% A: 95% B (3.5 min) to 5% A: 95% B (4 min)

LC/MS Method D: Column: Waters XBridge C18, 50×4.6 mm, 2.5 μm; flow: 1.3 ml/min; eluent A: water+0.1% FA; eluent B: ACN+0.1% FA; gradient: 97% A: 3% B (0 min) to 40% A: 60% B (3.5 min) to 2% A: 98% B (4 min) to 2% A: 98% B (5 min) to 97% A: 3% B (5.2 min) to 97% A: 3% B (6.5 min)

LC/MS Method E: Column: Merck Chromolith FastGrad RP-18e, 50×2 mm; flow: 2.4 ml/min; eluent A: water+0.05% TFA; eluent B: ACN+0.05% TFA; gradient: 98% A: 2% B (0.2 min) to 2% A: 98% B (2.4 min) to 2% A: 98% B (3.2 min) to 98% A: 2% B (3.3 min) to 98% A: 2% B (4 min)

LC/MS Method F: Column: Merck Chromolith FastGrad RP-18e, 50×2 mm; flow: 2.0 ml/min; eluent A: water+0.05% TFA; eluent B: ACN+0.05% TFA; gradient: 98% A: 2% B (0.2 min) to 2% A: 98% B (2.4 min) to 2% A: 98% B (3.2 min) to 98% A: 2% B (3.3 min) to 98% A: 2% B (4 min)

LC/MS Method G: Column: Waters UPLC BEH XBridge C18, 50×2.1 mm, 1.7 μm; eluent A: water+0.1% FA; eluent B: ACN+0.08% FA; gradient: 95% A: 5% B (0 min) to 5% A: 95% B (1.1 min) to 5% A: 95% B (1.7 min) to 95% A: 5% B (1.8 min) to 95% A: 5% B (2 min)

LC/MS Method H: Column: Waters XBridge C18, 50×4.6 mm, 2.5 μm; eluent A: water+0.1% FA; eluent B: ACN+0.08% FA; gradient: 97% A: 3% B (0 min) to 2% A: 98% B (18 min) to 2% A: 98% B (19 min) to 97% A: 3% B (19.5 min) to 97% A: 3% B (20 min)

LC/MS Method K: Column: Waters UPLC BEH C18, 50×2.1 mm, 1.7 μm; flow: 0.9 ml/min; temperature 55° C.; eluent A: water+0.1% FA; eluent B: ACN+0.08% FA; gradient: 95% A: 5% B (0 min) to 5% A: 95% B (1.1 min) to 5% A: 95% B (1.7 min) to 95% A: 5% B (1.8 min) to 95% A: 5% B (2 min)

LC/MS Method L: Column: YMC Pack Jsphere H80, 33×2.1 mm, 4 μm; eluent A: water+0.05% TFA; eluent B:

methanol+0.05% TFA; gradient: 98% A: 2% B (1 min) to 5% A: 95% B (5.0 min) to 5% A: 95% B (6.25 min)

EXEMPLARY SYNTHESIS EXAMPLES

A) 2-(Morpholine-4-carbonyl)-7-oxy-isothiazolo[5,4-b]pyridin-3-one a) Isothiazolo[5,4-b]pyridin-3-one

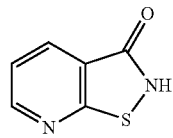

To a solution of diphenylphosphoryl azide (39.41 g, 0.139 mol) in pyridine (160 ml) and triethylamine (19 ml) was added 2-mercaptonicotinic acid (21.57 g, 0.139 mol) portionwise at 0° C. The reaction mixture was stirred overnight at room temperature and afterwards concentrated in vacuo. Ethanol (15 ml) was added at 30° C. to the crude product. Filtration at room temperature afforded a yellow solid which was washed with ethanol (15 ml) and dried in vacuo (10 mbar). 17.04 g (89%) of the title compound were obtained as light yellow solid.

b) 2-(Morpholine-4-carbonyl)-isothiazolo[5,4-b]pyridin-3-one

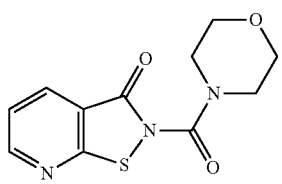 [SMILES: O=C(N1CCOCC1)n1sc2ncccc2c1=O]

To a suspension of isothiazolo[5,4-b]pyridin-3-one (5.0 g, 32.86 mmol) in acetonitrile (180 ml) was added dropwise triethylamine (14 ml, 99 mmol) and afterwards 4-morpholinecarbonyl chloride (3.8 ml, 32.9 mmol) at room temperature. The reaction mixture was stirred for 3 h at 60° C. The solvent was removed under reduced pressure. To the crude oil was added water (50 ml) and ethyl acetate (50 ml), the phases separated and the aqueous phase extracted with ethyl acetate. The organic layers were combined, washed with water, dried over sodium sulfate, filtered and concentrated in vacuo. Purification of the residue by high performance liquid chromatography (RP silica gel, acetonitrile/water/trifluoroacetic acid) and lyophilization of the product fractions provided 5.0 g (57%) of the title compound as a white powder.

c) 2-(Morpholine-4-carbonyl)-7-oxy-isothiazolo[5,4-b]pyridin-3-one

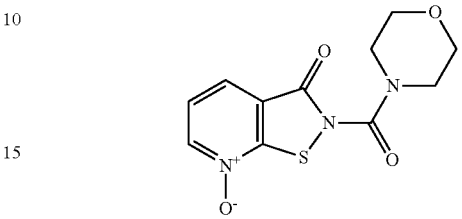

To a suspension of 2-(morpholine-4-carbonyl)-isothiazolo[5,4-b]pyridin-3-one (12.00 g, 45.22 mmol) in a mixture of methanol and water (600 ml, 1:1) was added potassium peroxomonosulfate (Oxone®, 41.71 g, 67.85 mmol) portionwise. The suspension was stirred at room temperature overnight. The solvent was removed in vacuo. The residue was dissolved in dichloromethane (250 ml) and washed with water (3×100 ml). The organic phase was dried over sodium sulfate, filtered and concentrated under reduced pressure. Purification of the residue by high performance liquid chromatography (RP silica gel, acetonitrile/water/trifluoroacetic acid) and lyophilization of the product fractions provided 8.0 g (63%) of the title compound as a white powder.

B) 2-(4-Acetyl-piperazine-1-carbonyl)-7-oxy-isothiazolo[5,4-b]pyridin-3-one a) 7-Oxy-isothiazolo[5,4-b]pyridin-3-one

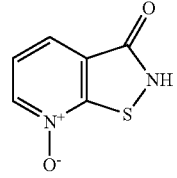 [SMILES: O=c1[nH]sc2c1ccc[n+]2[O-]]

To a solution of 2-(morpholine-4-carbonyl)-7-oxy-isothiazolo[5,4-b]pyridin-3-one (1.07 g, 3.80 mmol) in acetonitrile was added 2N aqueous sodium hydroxide (5 ml) dropwise at room temperature. The reaction mixture was stirred overnight and afterwards concentrated in vacuo to a volume of about 5 ml. Neutralization with aqueous 2N hydrochloric acid and filtration afforded the crude product which was dried at 45° C. under reduced pressure. Purification of the residue by high performance liquid chromatography (RP silica gel, acetonitrile/water/trifluoroacetic acid) and lyophilization of the product fractions provided 412 mg (64%) of the title compound as a white powder.

b) 2-(4-Acetyl-piperazine-1-carbonyl)-7-oxy-isothiazolo[5,4-b]pyridin-3-one

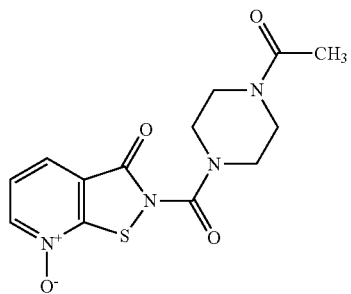 [SMILES: CC(=O)N1CCN(C(=O)n2sc3c(ccc[n+]3[O-])c2=O)CC1]

To a solution of 1-acetylpiperazine (46 mg, 0.36 mmol) in acetonitrile (3 ml) was added dropwise N-methylmorpholine (217 mg, 2.14 mmol) and afterwards a commercially available 20% solution of phosgene in toluene (140 mg, 28 mg (0.28 mmol) of phosgene) at room temperature. 7-Oxy-isothiazolo[5,4-b]pyridin-3-one (60 mg, 0.36 mmol) was added and stirring was continued for 3 h. The solvent was removed in vacuo and the residue was purified by high performance liquid chromatography (RP silica gel, acetonitrile/water/trifluoroacetic acid) to give 47 mg (41%) of the title compound as white powder In analogy to the procedures described above in the exemplary synthesis examples, the example compounds of the formula Ie listed in Table 1 were prepared. In Table 1, "Ex. no." means the number of the example compound; "LC/MS" means the LC/MS method described above which was used in the HPLC and MS characterization of the example compound; "MS" means the mass number (in amu) of the peak of the protonated molecular ion, i.e. the ion M+1, observed in the mass spectrum, unless specified otherwise; "Rt" means the HPLC retention time (in minutes). In the formulae of the groups —N(R10)-R11 in Table 1 the line crossed with the symbol ∿ represents the free bond via which the group —N(R10)-R11 is bonded to the carbon atom of the C=O group which is attached to the nitrogen atom in the 2-position of the isothiazole ring depicted in formula Ie. I.e., in the formula of the complete molecule the terminal endpoint of the line crossed with the said symbol ends at the carbon atom of the C=O group which is attached to the nitrogen atom in the 2-position of the isothiazole ring in formula Ie. If the group X in the example compounds in Table 1 is "N", the group X in formula Ie is =N—, i.e. the compound is a compound of the formula Ie-1, and if the group X in the example compounds in Table 1 is "N(O)", the group X in formula Ie is =N(O)—, i.e. the compound is a compound of the formula Ie-2.

TABLE 1

Example compounds of the formula Ie

| Ex. no. | X | —N(R10)(R11) | LC/MS | MS (M + 1) | Rt [min] |
|---|---|---|---|---|---|
| 1 | N | —N(piperazine)N—CH3 | A | 279.08 | 0.73 |
| 2 | N | —N(CH3)CH3 | A | 224.03 | 1.10 |
| 3 | N | —N(morpholine) | A | 266.06 | 1.09 |

TABLE 1-continued

Example compounds of the formula Ie

| Ex. no. | X | NR10R11 group | LC/MS | MS (M + 1) | Rt [min] |
|---|---|---|---|---|---|
| 4 | N | pyrrolidin-1-yl | B | 291.35(1) | 1.64 |
| 5 | N(O) | morpholin-4-yl | C | 282.01 | 1.92 |
| 6 | N | 4-(4-cyanophenyl)piperazin-1-yl | E | 366.20 | 1.98 |
| 7 | N | piperazin-1-yl | E | 265.09 | 0.79 |
| 8 | N | 4-(carboxymethyl)piperazin-1-yl | E | 323.09 | 0.75 |
| 9 | N(O) | 4-(4-cyanophenyl)piperazin-1-yl | E | 382.15 | 1.05 |
| 10 | N(O) | 4-(carboxymethyl)piperazin-1-yl | E | 339.12 | 0.90 |
| 11 | N | 2-carboxypyrrolidin-1-yl | E | 294.09 | 1.11 |
| 12 | N | 2-carboxypyrrolidin-1-yl | D | 294.03 | 2.88 |
| 13 | N(O) | 2-carboxypyrrolidin-1-yl | E | 310.09 | 0.93 |

TABLE 1-continued

Example compounds of the formula Ie

| Ex. no. | X | -N(R10)(R11) group | LC/MS | MS (M+1) | Rt [min] |
|---|---|---|---|---|---|
| 14 | N | piperazine-N-(2-carboxyphenyl) | E | 385.14 | 1.21 |
| 15 | N(O) | pyrrolidine-2-carboxylic acid | D | 309.96 | 2.29 |
| 16 | N(O) | NH-CH(CH3)-(2,3-dihydro-1,4-benzodioxin-6-yl) | E | 374.07 | 1.36 |
| 17 | N(O) | NH-CH(CH3)-(benzofuran-2-yl) | E | 356.06 | 1.49 |
| 18 | N(O) | NH-C(CH3)2-(3,4-dimethoxyphenyl) | E | 390.1 | 1.36 |
| 19 | N | piperazine-N-(2-cyanophenyl) | E | 366.07 | 1.50 |
| 20 | N | piperazine-N-C(O)-CH2-O-phenyl | F | 413.15 | 1.53 |
| 21 | N(O) | piperazine-N-C(O)-CH2-O-phenyl | G | 429.21 | 1.03 |
| 22 | N | peracetylated aminosugar | G | 548.16(2) | 1.09 |

TABLE 1-continued

Example compounds of the formula Ie

| Ex. no. | X | –N(R10)(R11) | LC/MS | MS (M + 1) | Rt [min] |
|---|---|---|---|---|---|
| 23 | N | (aminomethyl pyranose triol, HO, OH, OH, OH) | F | 358.11 | 0.98 |
| 24 | N(O) | –NH–CH2–(3,4-dimethoxyphenyl) | H | 362.15 | 6.61 |
| 25 | N(O) | (aminomethyl pyranose triol, HO, OH, OH, OH) | D | 374.18 | 1.46 |
| 26 | N | piperazine-N-C(O)CH3 | D | 307.12 | 2.69 |
| 27 | N | piperazine-N-C(O)-cyclopropyl | D | 333.17 | 3.12 |
| 28 | N(O) | piperazine-N-C(O)-cyclopropyl | K | 349.18 | 0.89 |
| 29 | N(O) | piperazine-N-C(O)CH(CH3)2 | D | 351.24 | 2.58 |
| 30 | N | piperazine-N-C(O)-(pyridin-4-yl N-oxide) | K | 386.19 | 0.88 |
| 31 | N | piperazine-N-C(O)-(pyridin-3-yl N-oxide) | K | 386.20 | 0.90 |

TABLE 1-continued

Example compounds of the formula Ie

| Ex. no. | X | NR10R11 group | LC/MS | MS (M+1) | Rt [min] |
|---|---|---|---|---|---|
| 32 | N | piperazine-C(O)-pyridine N-oxide | K | 386.14 | 0.91 |
| 33 | N(O) | NH-piperidine (4-amino via ring NH) | K | 295.22 | 0.27 |
| 34 | N(O) | 4-aminopiperidin-1-yl | D | 295.16 | 1.07 |
| 35 | N | piperazine-C(O)C(O)NH2 | K | 336.19 | 0.88 |
| 36 | N | piperazine-SO2-CH2CH3 | K | 357.16 | 1.07 |
| 37 | N(O) | piperazine-C(O)C(O)NH2 | K | 351.99 | 0.67 |
| 38 | N(O) | piperazine-SO2-CH2CH3 | D | 373.2 | 2.60 |
| 39 | N(O) | piperazine-SO2-CH3 | D | 359.1 | 2.37 |
| 40 | N(O) | 4-(4-methylpiperazin-1-yl)piperidin-1-yl | D | 378.27 | 1.46 |
| 41 | N(O) | N(CH2CH2OCH3)2 | K | 328.15 | 0.94 |

TABLE 1-continued

Example compounds of the formula Ie

| Ex. no. | X | -N(R10)(R11) | LC/MS | MS (M+1) | Rt [min] |
|---|---|---|---|---|---|
| 42 | N(O) | piperidine-N(H)CH3 | D | 309.13 | 1.41 |
| 43 | N(O) | N(CH3)CH2CH2NH2 | D | 269.16 | 1.02 |
| 44 | N(O) | piperazine-C(O)CH2NH2 | K | 338.18 | 0.27 |
| 45 | N(O) | 1,8-diazaspiro[4.5]decane | K | 335.19 | 0.35 |
| 46 | N(O) | piperazine-pyridazine-pyrrolidine | D | 428.25 | 2.11 |
| 47 | N(O) | piperazine-pyridazine-NHS(O)2CH3 | K | 452.14 | 0.80 |
| 48 | N(O) | piperazine-(Cl,N-CH3-pyridazinone) | K | 423.13 | 0.89 |
| 49 | N(O) | piperazine-triazinedione | K | 390.24(3) | 0.75 |
| 50 | N(O) | piperazine-C(O)-prolinyl | D | 378.21 | 1.54 |
| 51 | N(O) | piperazine-C(O)CH2NHC(O)CH2NH2 | D | 395.17 | 1.34 |
| 52 | N(O) | piperazine-C(O)-(2-aminocyclopentyl) | K | 392.18 | 0.66 |

TABLE 1-continued
Example compounds of the formula Ie
| Ex. no. | X | (structure with R10/R11) | LC/MS | MS (M+1) | Rt [min] |
|---|---|---|---|---|---|
| 53 | N(O) | 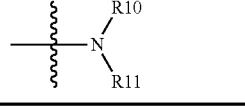 | K | 281.07 | 0.20 |
| 54 | N(O) | 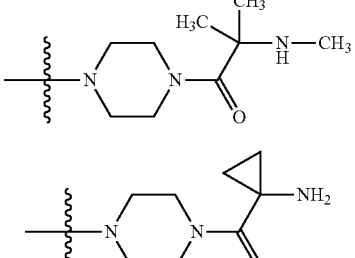 | K | 364.1 | 0.52 |
| 55 | N(O) | 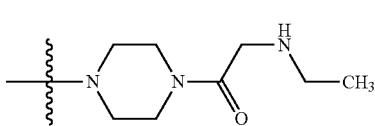 [SMILES: *N1CCN(C(=O)CNCC)CC1] | K | 366.07 | 0.60 |
| 56 | N(O) | 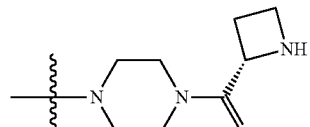 | K | 364.1 | 0.41 |
| 57 | N(O) | 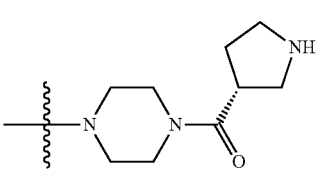 [SMILES: *N1CCN(C(=O)[C@@H]2CCNC2)CC1] | K | 378.14 | 0.34 |
| 58 | N(O) | 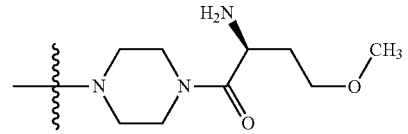 [SMILES: *N1CCN(C(=O)[C@@H](N)CCOC)CC1] | K | 396.12 | 0.60 |
| 59 | N(O) | 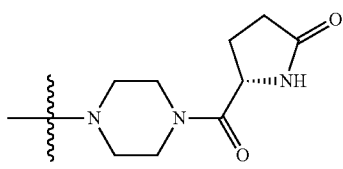 [SMILES: *N1CCN(C(=O)[C@@H]2CCC(=O)N2)CC1] | K | 392.07 | 0.68 |
| 60 | N(O) | 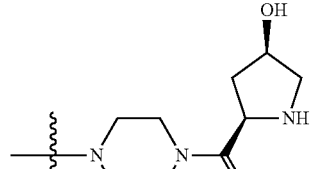 | K | 394.1 | 0.39 |
| 61 | N(O) | 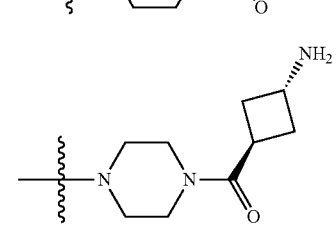 | K | 378.09 | 0.48 |

TABLE 1-continued

Example compounds of the formula Ie

| Ex. no. | X | -N(R10)(R11) group | LC/MS | MS (M+1) | Rt [min] |
|---|---|---|---|---|---|
| 62 | N(O) | 1-(2-oxoimidazolidin-1-yl)piperidin-4-yl | K | 364.12 | 0.77 |
| 63 | N(O) | 4-(sulfamoyl)piperazin-1-yl | K | 358.15(3) | 0.69 |
| 64 | N(O) | 3-aminopyrrolidin-1-yl | D | 281.06 | 0.80 |
| 65 | N(O) | 3,4-dihydroquinoxalin-1(2H)-yl | K | 329.09 | 0.97 |
| 66 | N(O) | N-methyl-N-(tetrahydro-2H-pyran-4-yl)amino | K | 310.1 | 0.84 |
| 67 | N(O) | (tetrahydro-2H-pyran-4-yl)amino | K | 296.1 | 0.89 |
| 68 | N | 4-(3,4-dimethoxybenzoyl)piperazin-1-yl | F | 429.15 | 1.38 |
| 69 | N(O) | 4-(3,4-dimethoxybenzoyl)piperazin-1-yl | L | 445.13 | 2.77 |
| 70 | N(O) | 4-acetylpiperazin-1-yl | K | 323.18 | 0.74 |

TABLE 1-continued

Example compounds of the formula Ie

| Ex. no. | X | -N(R10)(R11) | LC/MS | MS (M+1) | Rt [min] |
|---|---|---|---|---|---|
| 71 | N(O) | piperazine-N-C(O)- linked to 3-oxo-isothiazolo[5,4-b]pyridine 7-N-oxide | K | 475.2 | 0.85 |
| 72 | N(O) | piperazinyl (NH) | D | 281.06 | 0.82 |
| 73 | N(O) | NH-C(CN)(cyclopropyl) | D | 277.03 | 2.31 |
| 74 | N(O) | 4-(pyridine-4-carbonyl)piperazin-1-yl | D | 386.14 | 1.94 |
| 75 | N(O) | 4-(3-methylbutanoyl)piperazin-1-yl | K | 365.14 | 0.96 |
| 76 | N(O) | -NH-CH2CH2-NH-C(O)CH3 | K | 297.13 | 0.66 |
| 77 | N(O) | 4-benzoylpiperazin-1-yl | K | 385.27 | 0.93 |
| 78 | N(O) | 4-(butanoyl)piperidin-1-yl | K | 350.17 | 1.08 |
| 79 | N(O) | 4-carbamoylpiperidin-1-yl | K | 323.15 | 0.49 |
| 80 | N(O) | 3-oxopiperazin-1-yl | K | 295.09 | 0.61 |

TABLE 1-continued

Example compounds of the formula Ie

| Ex. no. | X | (structure) | LC/MS | MS (M + 1) | Rt [min] |
|---|---|---|---|---|---|
| 81 | N(O) | 2,6-dimethylmorpholine | K | 310.17 | 0.89 |
| 82 | N(O) | NH-CH2CH2-NH2 | D | 269.16 | 1.29 |
| 83 | N(O) | piperazine-C(O)-CH2-O-CH3 | K | 367.06 | 0.66 |
| 84 | N(O) | piperazine-C(O)-NH2 | K | 324.1 | 0.45 |
| 85 | N | piperazine-S(O)2-NH2 | K | 344.1 | 0.95 |
| 86 | N(O) | 4-hydroxypiperidine | K | 296.1 | 0.67 |
| 87 | N(O) | 3-(piperazin-1-yl)pyrrolidine | K | 350.2 | 0.40 |
| 88 | N | piperazine-S(O)2-CH3 | K | 343.17 | 1.02 |
| 89 | N(O) | piperazine-C(O)-pyridin-2-yl | K | 386.22 | 0.86 |
| 90 | N(O) | piperazine-C(O)-CH2-NH2 | K | | |
| 91 | N(O) | piperazine-C(O)-CH(NH2)-CH2-CN | K | 377.15 | 0.42 |

TABLE 1-continued

Example compounds of the formula Ie

| Ex. no. | X | NR10R11 group | LC/MS | MS (M + 1) | Rt [min] |
|---|---|---|---|---|---|
| 92 | N(O) | piperazine-carbonyl-(3-aminocyclopentyl) | K | 392.14 | 0.59 |
| 93 | N(O) | piperazine-carbonyl-pyrrolidinyl | K | 378.17 | 0.40 |
| 94 | N | piperazin-2-one-yl | K | 279.29 | 0.87 |

(1) M + H + CH$_3$CN (2) M + Na (3) M − 1 (ionization method ES-)

PHARMACOLOGICAL EXAMPLES a) Assay Method for the Quantification of TGM2 Transglutaminase Inhibitory Activity The activity of the compounds for inhibition of TGM2 was determined with recombinant human TGM2 (Zedira GmbH, Darmstadt, Germany, Product Nr. T002) and the peptidic compound H-Abz-APE(CAD-DNP)QEA-OH as substrate (Zedira GmbH, Darmstadt, Germany, Product Nr. A102; CAD-DNP is N$^\omega$-2,4-dinitrophenyl-cadaverine, i.e. the carboxylic acid group in the side chain of the respective glutamyl moiety is amidated with the primary amino group of N-(2,4-dinitrophenyl)pentane-1,5-diamine; cf. also K. Oertel et al., Anal. Biochem. 2007, 367: 152-158). For this purpose, 2 µl of a solution of different concentrations of the test compound in dimethyl sulfoxide was added to 28 µl of buffer (50 mM TRIS, 100 mM NaCl, 10 mM CaCl$_2$, pH 7.5) and 10 µl of a TGM2 solution to give a TMG2 test concentration of 25 µg/ml, and the mixture incubated for 15 minutes at room temperature in a 96 half-well microtiter plate. The enzyme reaction was started by the addition of 10 µl of substrate solution containing H-Abz-APE(CAD-DNP)QEA-OH and glycine methyl ester hydrochloride in buffer to give test concentrations of H-Abz-APE(CAD-DNP)QEA-OH of 50 µM and of glycine methyl ester hydrochloride of 5 mM. The time course of the reaction was monitored with excitation at 318 nm and measurement at emission wavelength 418 nm in a microtiter plate reader (SpectraMax M5, Molecular Devices) over 15 minutes. Rates were calculated from the linear part of the curve (generally between 5 and 10 minutes). IC$_{50}$ values were calculated from the means (duplicates) of a dilution series of the compound, using the software Softmax Pro (Version 4.8, Molecular Devices). Results (IC$_{50}$ values in micromol/liter) obtained with compounds of the invention are given in Table 2.

TABLE 2

IC$_{50}$ values for inhibition of TGM2

| Example number | IC$_{50}$ [µmol/l] |
|---|---|
| 5 | 0.27 |
| 6 | 1.1 |
| 8 | 18 |
| 10 | 12 |
| 16 | 26 |
| 20 | 0.11 |
| 21 | 0.014 |
| 22 | 1.4 |
| 23 | 0.8 |
| 24 | 0.37 |
| 26 | 0.34 |
| 27 | 0.42 |
| 28 | 0.045 |
| 29 | 0.062 |
| 36 | 0.43 |
| 38 | 0.061 |
| 40 | 0.34 |
| 42 | 0.24 |
| 44 | 0.12 |
| 45 | 4.3 |
| 46 | 0.14 |
| 50 | 2.3 |
| 53 | 1.7 |
| 55 | 2.0 |
| 59 | 1.0 |
| 62 | 3.1 |
| 63 | 2.6 |
| 68 | 0.065 |
| 69 | 0.054 |
| 70 | 0.062 |
| 72 | 1.2 |
| 74 | 0.13 |
| 78 | 0.12 |
| 80 | 0.15 |
| 81 | 2.9 |
| 83 | 0.75 |

TABLE 2-continued

IC$_{50}$ values for inhibition of TGM2

| Example number | IC$_{50}$ [µmol/l] |
|---|---|
| 84 | 1.7 |
| 85 | 0.20 |
| 86 | 2.1 |
| 88 | 0.25 |
| 89 | 0.072 |

What is claimed is:

1. A compound of the formula I, in any of its stereoisomeric forms or a mixture of stereoisomeric forms in any ratio, or a pharmaceutically acceptable salt thereof,

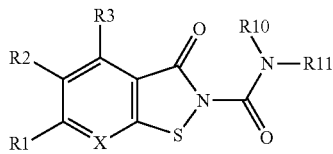

wherein

X is selected from the series consisting of =N— and =N(O)—;

R1, R2 and R3 are independently of one another selected from the series consisting of hydrogen, halogen, (C$_1$-C$_4$)-alkyl, (C$_1$-C$_4$)-alkyl-O—, nitro, cyano, (C$_1$-C$_4$)-alkyl-O—C(O)—, R4-N(R5)-C(O)— and R6-N(R7)-S(O)$_2$—;

R4 is selected from the series consisting of hydrogen, (C$_1$-C$_4$)-alkyl, (C$_3$-C$_7$)-cycloalkyl, (C$_3$-C$_7$)-cycloalkyl-(C$_1$-C$_4$)-alkyl-, phenyl, phenyl-(C$_1$-C$_4$)-alkyl-, Het1 and Het1-(C$_1$-C$_4$)-alkyl-, wherein Het1 is optionally substituted by one or more identical or different substituents R8;

R5, R6 and R7 are independently of one another selected from the series consisting of hydrogen, (C$_1$-C$_4$)-alkyl, (C$_3$-C$_7$)-cycloalkyl and (C$_3$-C$_7$)-cycloalkyl-(C$_1$-C$_4$)-alkyl-;

R8 is selected from the series consisting of halogen, (C$_1$-C$_4$)-alkyl, hydroxy, oxo, (C$_1$-C$_4$)-alkyl-O— and cyano;

R10 is selected from the series consisting of hydrogen, (C$_1$-C$_4$)-alkyl, (C$_3$-C$_7$)-cycloalkyl, (C$_3$-C$_7$)-cycloalkyl-(C$_1$-C$_4$)-alkyl- and (C$_1$-C$_4$)-alkyl-O—(C$_1$-C$_4$)-alkyl-, with the proviso that R10 can only be hydrogen if X is =N(O)—;

R11 is selected from the series consisting of (C$_1$-C$_4$)-alkyl which is optionally substituted by one or more identical or different substituents R12, (C$_3$-C$_7$)-cycloalkyl which is optionally substituted by one or more identical or different substituents R13, and Het2 which is optionally substituted by one or more identical or different substituents R14 and wherein Het2 is bonded via a ring carbon atom;

or the groups R10 and R11, together with the nitrogen atom carrying them, form a 4-membered to 12-membered, monocyclic or bicyclic, saturated or partially unsaturated heterocycle which, in addition to the nitrogen atom carrying R10 and R11, comprises 0, 1 or 2 further ring heteroatoms selected from the series consisting of nitrogen, oxygen and sulfur, which is optionally substituted on ring carbon atoms by one or more identical or different substituents R30, and which is optionally substituted on further ring nitrogen atoms by one or more identical or different substituents R40;

R12 is selected from the series consisting of (C$_3$-C$_7$)-cycloalkyl, phenyl, Het3, hydroxy, (C$_1$-C$_4$)-alkyl-O—, (C$_1$-C$_4$)-alkyl-C(O)—O—, R15-N(R16)- and R17-C(O)—N(R18)-, wherein phenyl and Het3 independently of one another are optionally substituted by one or more identical or different substituents R19;

R13 is selected from the series consisting of hydroxy, (C$_1$-C$_4$)-alkyl-O—, (C$_1$-C$_4$)-alkyl-C(O)—O— and cyano;

R14 is selected from the series consisting of fluorine, (C$_1$-C$_4$)-alkyl, hydroxy, (C$_1$-C$_4$)-alkyl-O—, (C$_1$-C$_4$)-alkyl-C(O)—O—, HO—(C$_1$-C$_4$)-alkyl-, (C$_1$-C$_4$)-alkyl-O—(C$_1$-C$_4$)-alkyl-, (C$_1$-C$_4$)-alkyl-C(O)—O—(C$_1$-C$_4$)-alkyl- and (C$_1$-C$_4$)-alkyl-C(O)—;

R15, R16 and R18 are independently of one another selected from the series consisting of hydrogen, (C$_1$-C$_4$)-alkyl, (C$_3$-C$_7$)-cycloalkyl and (C$_3$-C$_7$)-cycloalkyl-(C$_1$-C$_4$)-alkyl-;

R17 is selected from the series consisting of (C$_1$-C$_4$)-alkyl, (C$_3$-C$_7$)-cycloalkyl, (C$_3$-C$_7$)-cycloalkyl-(C$_1$-C$_4$)-alkyl-, phenyl and phenyl-(C$_1$-C$_4$)-alkyl-;

R19 is selected from the series consisting of halogen, (C$_1$-C$_4$)-alkyl, hydroxy, (C$_1$-C$_4$)-alkyl-O—, (C$_1$-C$_4$)-alkyl-C(O)—O—, cyano, R20-O—C(O)— and R21-N(R22)-C(O)—;

R20, R21 and R22 are independently of one another selected from the series consisting of hydrogen and (C$_1$-C$_4$)-alkyl;

R30 is selected from the series consisting of fluorine, (C$_1$-C$_4$)-alkyl, Het2, hydroxy, oxo, (C$_1$-C$_4$)-alkyl-O—, R31-N(R32)-, (C$_1$-C$_4$)-alkyl-C(O)—, R33-O—C(O)— and R34-N(R35)-C(O)—, wherein Het2 is optionally substituted by one or more identical or different substituents R36;

R31, R32, R33, R34 and R35 are independently of one another selected from the series consisting of hydrogen and (C$_1$-C$_4$)-alkyl;

R36 is selected from the series consisting of fluorine, (C$_1$-C$_4$)-alkyl, hydroxy and oxo;

R40 is selected from the series consisting of (C$_1$-C$_4$)-alkyl which is optionally substituted by one or more identical or different substituents R41, (C$_3$-C$_7$)-cycloalkyl which is optionally substituted by one or more identical or different substituents R42, phenyl which is optionally substituted by one or more identical or different substituents R43, Het1 which is optionally substituted by one or more identical or different substituents R44, (C$_1$-C$_4$)-alkyl-C(O)— which is optionally substituted by one or more identical or different substituents R45, (C$_3$-C$_7$)-cycloalkyl-C(O)— which is optionally substituted by one or more identical or different substituents R46, phenyl-C(O)— which is optionally substituted by one or more identical or different substituents R47, Het3-C(O)— which is optionally substituted by one or more identical or different substituents R48 and wherein Het3 is bonded via a ring carbon atom, R49-N(R50)-C(O)—, (C$_1$-C$_4$)-alkyl-S(O)$_2$— and R51-N(R52)-S(O)$_2$—;

R41 is selected from the series consisting of (C$_3$-C$_7$)-cycloalkyl, hydroxy, (C$_1$-C$_4$)-alkyl-O—, R60-N(R61)-, R62-O—C(O)— and R63-N(R64)-C(O)—;

R42 is selected from the series consisting of hydroxy and R65-N(R66)-;

R43 is selected from the series consisting of halogen, (C$_1$-C$_4$)-alkyl, hydroxy, (C$_1$-C$_4$)-alkyl-O—, cyano, R67-O—C(O)— and R68-N(R69)-C(O)—;

R44 is selected from the series consisting of halogen, ($C_1$-$C_4$)-alkyl, hydroxy, oxo, ($C_1$-$C_4$)-alkyl-O—, R70-N(R71)-, ($C_1$-$C_4$)-alkyl-C(O)—N(R72)-, ($C_1$-$C_4$)-alkyl-S(O)$_2$—N(R73)- and Het4, wherein Het4 is optionally substituted by one or more identical or different substituents R74;

R45 is selected from the series consisting of ($C_3$-$C_7$)-cycloalkyl, cyano, hydroxy, ($C_1$-$C_4$)-alkyl-O—, phenyl-O—, phenyl-($C_1$-$C_4$)-alkyl-O—, oxo, R75-N(R76)- and R77-C(O)—N(R78)-;

R46 is selected from the series consisting of hydroxy and R79-N(R80)-;

R47 is selected from the series consisting of halogen, ($C_1$-$C_4$)-alkyl, ($C_1$-$C_4$)-alkyl-O— and R81-N(R82)-C(O)—;

R48 is selected from the series consisting of halogen, ($C_1$-$C_4$)-alkyl, hydroxy, oxo and ($C_1$-$C_4$)-alkyl-O—;

R49 and R51 are independently of one another selected from the series consisting of hydrogen, ($C_1$-$C_4$)-alkyl, ($C_3$-$C_7$)-cycloalkyl, ($C_3$-$C_7$)-cycloalkyl-($C_1$-$C_4$)-alkyl-, phenyl and phenyl-($C_1$-$C_4$)-alkyl-;

R50 and R52 are independently of one another selected from the series consisting of hydrogen, ($C_1$-$C_4$)-alkyl, ($C_3$-$C_7$)-cycloalkyl and ($C_3$-$C_7$)-cycloalkyl-($C_1$-$C_4$)-alkyl-;

R60, R61, R62, R63, R64, R65, R66, R67, R68, R69, R70, R71, R72, R73, R76, R78, R79, R80, R81, R82, R83 and R84 are independently of one another selected from the series consisting of hydrogen and ($C_1$-$C_4$)-alkyl;

R74 is selected from the series consisting of fluorine and ($C_1$-$C_4$)-alkyl;

R75 is selected from the series consisting of hydrogen, ($C_1$-$C_4$)-alkyl, ($C_3$-$C_7$)-cycloalkyl, ($C_3$-$C_7$)-cycloalkyl-($C_1$-$C_4$)-alkyl-, phenyl and phenyl-($C_1$-$C_4$)-alkyl-;

R77 is selected from the series consisting of ($C_1$-$C_4$)-alkyl and R83-N(R84)-($C_1$-$C_4$)-alkyl-;

Het1 is a monocyclic, 4-membered to 7-membered, saturated, partially unsaturated or aromatic heterocycle which comprises 1, 2 or 3 identical or different ring heteroatoms selected from the series consisting of nitrogen oxygen and sulfur, and which is bonded via a ring carbon atom;

Het2 is a monocyclic, 4-membered to 7-membered, saturated heterocycle which comprises 1 or 2 identical or different ring heteroatoms selected from the series consisting of nitrogen, oxygen and sulfur;

Het3 is a monocyclic or bicyclic, 4-membered to 12-membered, saturated, partially unsaturated or aromatic heterocycle which comprises 1, 2 or 3 identical or different ring heteroatoms selected from the series consisting of nitrogen, oxygen and sulfur;

Het4 is a monocyclic, 4-membered to 7-membered, saturated heterocycle which comprises a ring nitrogen atom via which Het4 is bonded, and 0 or 1 further ring heteroatom selected from the series consisting of nitrogen, oxygen and sulfur;

wherein all phenyl groups are optionally substituted by one or more identical or different substituents selected from the series consisting of halogen, ($C_1$-$C_4$)-alkyl, cyano, hydroxy and ($C_1$-$C_4$)-alkyl-O—, unless specified otherwise;

wherein all cycloalkyl groups, independently of any other substituents which can be present on a cycloalkyl group, are optionally substituted by one or more identical or different substituents selected from the series consisting of fluorine and ($C_1$-$C_4$)-alkyl;

wherein all alkyl groups, independently of any other substituents which can be present on an alkyl group, are optionally substituted by one or more fluorine substituents;

with the proviso that the compound of the formula I is not 3-oxo-3H-isothiazolo[5,4-b]pyridine-2-carboxylic acid diethylamide.

2. The compound of the formula I, in any of its stereoisomeric forms or a mixture of stereoisomeric forms in any ratio, or a pharmaceutically acceptable salt thereof, according to claim 1, wherein X is =N(O)—.

3. The compound of the formula I, in any of its stereoisomeric forms or a mixture of stereoisomeric forms in any ratio, or a pharmaceutically acceptable salt thereof, according to claim 1, wherein R1, R2 and R3 are independently of one another selected from the series consisting of hydrogen, halogen, ($C_1$-$C_4$)-alkyl, nitro, cyano, ($C_1$-$C_4$)-alkyl-O—C(O)— and R4-N(R5)-C(O)—.

4. The compound of the formula I, in any of its stereoisomeric forms or a mixture of stereoisomeric forms in any ratio, or a pharmaceutically acceptable salt thereof, according to claim 2, wherein R1, R2 and R3 are independently of one another selected from the series consisting of hydrogen, halogen, ($C_1$-$C_4$)-alkyl, nitro, cyano, ($C_1$-$C_4$)-alkyl-O—C(O)— and R4-N(R5)-C(O)—.

5. The compound of the formula I, in any of its stereoisomeric forms or a mixture of stereoisomeric forms in any ratio, or a pharmaceutically acceptable salt thereof, according to claim 1, wherein R1, R2 and R3 are independently of one another selected from the series consisting of hydrogen, halogen, ($C_1$-$C_4$)-alkyl and cyano.

6. The compound of the formula I, in any of its stereoisomeric forms or a mixture of stereoisomeric forms in any ratio, or a pharmaceutically acceptable salt thereof, according to claim 2, wherein R1, R2 and R3 are independently of one another selected from the series consisting of hydrogen, halogen, ($C_1$-$C_4$)-alkyl and cyano.

7. The compound of the formula I, in any of its stereoisomeric forms or a mixture of stereoisomeric forms in any ratio, or a pharmaceutically acceptable salt thereof, according to claim 1, wherein R10 is selected from the series consisting of ($C_1$-$C_4$)-alkyl, ($C_3$-$C_7$)-cycloalkyl, ($C_3$-$C_7$)-cycloalkyl-($C_1$-$C_4$)-alkyl- and ($C_1$-$C_4$)-alkyl-O—($C_1$-$C_4$)-alkyl-.

8. The compound of the formula I, in any of its stereoisomeric forms or a mixture of stereoisomeric forms in any ratio, or a pharmaceutically acceptable salt thereof, according to claim 2, wherein R10 is selected from the series consisting of ($C_1$-$C_4$)-alkyl, ($C_3$-$C_7$)-cycloalkyl, ($C_3$-$C_7$)-cycloalkyl-($C_1$-$C_4$)-alkyl- and ($C_1$-$C_4$)-alkyl-O—($C_1$-$C_4$)-alkyl-.

9. The compound of the formula I, in any of its stereoisomeric forms or a mixture of stereoisomeric forms in any ratio, or a pharmaceutically acceptable salt thereof, according to claim 5, wherein R10 is selected from the series consisting of ($C_1$-$C_4$)-alkyl, ($C_3$-$C_7$)-cycloalkyl, ($C_3$-$C_7$)-cycloalkyl-($C_1$-$C_4$)-alkyl- and ($C_1$-$C_4$)-alkyl-O—($C_1$-$C_4$)-alkyl-.

10. The compound of the formula I, in any of its stereoisomeric forms or a mixture of stereoisomeric forms in any ratio, or a pharmaceutically acceptable salt thereof, according to claim 1, wherein X is =N(O)—;

R1, R2 and R3 are independently of one another selected from the series consisting of hydrogen, halogen, ($C_1$-$C_4$)-alkyl and cyano;

R10 is selected from the series consisting of ($C_1$-$C_4$)-alkyl, ($C_3$-$C_7$)-cycloalkyl, ($C_3$-$C_7$)-cycloalkyl-($C_1$-$C_4$)-alkyl- and ($C_1$-$C_4$)-alkyl-O—($C_1$-$C_4$)-alkyl-.

11. The compound of the formula I, in any of its stereoisomeric forms or a mixture of stereoisomeric forms in any ratio, or a pharmaceutically acceptable salt thereof, according to claim 1, wherein X is selected from the series consisting of =N— and =N(O)—;

R1, R2 and R3 are independently of one another selected from the series consisting of hydrogen, halogen, ($C_1$-$C_4$)-alkyl, cyano, ($C_1$-$C_4$)-alkyl-O—C(O)— and R4-N(R5)-C(O)—;

R4 is selected from the series consisting of hydrogen, ($C_1$-$C_4$)-alkyl, ($C_3$-$C_7$)-cycloalkyl and ($C_3$-$C_7$)-cycloalkyl-($C_1$-$C_4$)-alkyl-;

R5 is selected from the series consisting of hydrogen and ($C_1$-$C_4$)-alkyl;

R10 is selected from the series consisting of hydrogen, ($C_1$-$C_4$)-alkyl, ($C_3$-$C_7$)-cycloalkyl, ($C_3$-$C_7$)-cycloalkyl-($C_1$-$C_4$)-alkyl- and ($C_1$-$C_4$)-alkyl-O—($C_1$-$C_4$)-alkyl-, with the proviso that R10 can only be hydrogen if X is =N(O)—;

R11 is selected from the series consisting of ($C_1$-$C_4$)-alkyl which is optionally substituted by one or more identical or different substituents R12, ($C_3$-$C_7$)-cycloalkyl which is optionally substituted by one or more identical or different substituents R13, and Het2 which is optionally substituted by one or more identical or different substituents R14 and wherein Het2 is bonded via a ring carbon atom;

or the groups R10 and R11, together with the nitrogen atom carrying them, form a 4-membered to 10-membered, monocyclic or bicyclic, saturated or partially unsaturated heterocycle which, in addition to the nitrogen atom carrying R10 and R11, comprises 0 or 1 further ring heteroatoms selected from the series consisting of nitrogen, oxygen and sulfur, which is optionally substituted on ring carbon atoms by one or more identical or different substituents R30, and which is optionally substituted on further ring nitrogen atoms by one or more identical or different substituents R40;

R12 is selected from the series consisting of phenyl, Het3, hydroxy, ($C_1$-$C_4$)-alkyl-O—, R15-N(R16)- and R17-C(O)—N(R18)-, wherein phenyl and Het3 independently of one another are optionally substituted by one or more identical or different substituents R19;

R13 is selected from the series consisting of hydroxy, ($C_1$-$C_4$)-alkyl-O— and cyano;

R14 is selected from the series consisting of ($C_1$-$C_4$)-alkyl, hydroxy, ($C_1$-$C_4$)-alkyl-C(O)—O—, HO—($C_1$-$C_4$)-alkyl-, ($C_1$-$C_4$)-alkyl-C(O)—O—($C_1$-$C_4$)-alkyl- and ($C_1$-$C_4$)-alkyl-C(O)—;

R15, R16 and R18 are independently of one another selected from the series consisting of hydrogen and ($C_1$-$C_4$)-alkyl;

R17 is selected from the series consisting of ($C_1$-$C_4$)-alkyl, ($C_3$-$C_7$)-cycloalkyl and ($C_3$-$C_7$)-cycloalkyl-($C_1$-$C_4$)-alkyl-;

R19 is selected from the series consisting of halogen, ($C_1$-$C_4$)-alkyl, hydroxy, ($C_1$-$C_4$)-alkyl-O—, ($C_1$-$C_4$)-alkyl-C(O)—O—;

R30 is selected from the series consisting of fluorine, ($C_1$-$C_4$)-alkyl, Het2, hydroxy, oxo, ($C_1$-$C_4$)-alkyl-O—, R31-N(R32)-, ($C_1$-$C_4$)-alkyl-C(O)—, R33-O—C(O)— and R34-N(R35)-C(O)—, wherein Het2 is optionally substituted by one or more identical or different substituents R36;

R31, R32, R33, R34 and R35 are independently of one another selected from the series consisting of hydrogen and ($C_1$-$C_4$)-alkyl;

R36 is selected from the series consisting of fluorine, ($C_1$-$C_4$)-alkyl, hydroxy and oxo;

R40 is selected from the series consisting of ($C_1$-$C_4$)-alkyl which is optionally substituted by one or more identical or different substituents R41, ($C_3$-$C_7$)-cycloalkyl which is optionally substituted by one or more identical or different substituents R42, phenyl which is optionally substituted by one or more identical or different substituents R43, Het1 which is optionally substituted by one or more identical or different substituents R44, ($C_1$-$C_4$)-alkyl-C(O)— which is optionally substituted by one or more identical or different substituents R45, ($C_3$-$C_7$)-cycloalkyl-C(O)— which is optionally substituted by one or more identical or different substituents R46, phenyl-C(O)— which is optionally substituted by one or more identical or different substituents R47, Het3-C(O)— which is optionally substituted by one or more identical or different substituents R48 and wherein Het3 is bonded via a ring carbon atom, R49-N(R50)-C(O)—, ($C_1$-$C_4$)-alkyl-S(O)$_2$— and R51-N(R52)-S(O)$_2$—;

R41 is selected from the series consisting of ($C_1$-$C_4$)-alkyl-O—, R60-N(R61)-, R62-O—C(O)— and R63-N(R64)-C(O)—;

R42 is selected from the series consisting of R65-N(R66)-;

R43 is selected from the series consisting of halogen, ($C_1$-$C_4$)-alkyl, ($C_1$-$C_4$)-alkyl-O—, cyano, R67-O—C(O)— and R68-N(R69)-C(O)—;

R44 is selected from the series consisting of halogen, ($C_1$-$C_4$)-alkyl, hydroxy, oxo, ($C_1$-$C_4$)-alkyl-S(O)$_2$—N(R73)- and Het4, wherein Het4 is optionally substituted by one or more identical or different substituents R74;

R45 is selected from the series consisting of cyano, ($C_1$-$C_4$)-alkyl-O—, phenyl-O—, phenyl-($C_1$-$C_4$)-alkyl-O—, oxo, R75-N(R76)- and R77-C(O)—N(R78)-;

R46 is selected from the series consisting of R79-N(R80)-;

R47 is selected from the series consisting of halogen, ($C_1$-$C_4$)-alkyl, ($C_1$-$C_4$)-alkyl-O— and R81-N(R82)-C(O)—;

R48 is selected from the series consisting of halogen, ($C_1$-$C_4$)-alkyl, hydroxy and oxo;

R49 and R51 are independently of one another selected from the series consisting of hydrogen, ($C_1$-$C_4$)-alkyl, ($C_3$-$C_7$)-cycloalkyl and ($C_3$-$C_7$)-cycloalkyl-($C_1$-$C_4$)-alkyl-;

R50 and R52 are independently of one another selected from the series consisting of hydrogen and ($C_1$-$C_4$)-alkyl;

R60, R61, R62, R63, R64, R65, R66, R67, R68, R69, R73, R76, R78, R79, R80, R81, R82, R83 and R84 are independently of one another selected from the series consisting of hydrogen and ($C_1$-$C_4$)-alkyl;

R74 is selected from the series consisting of fluorine and ($C_1$-$C_4$)-alkyl;

R75 is selected from the series consisting of hydrogen, ($C_1$-$C_4$)-alkyl, ($C_3$-$C_7$)-cycloalkyl and ($C_3$-$C_7$)-cycloalkyl-($C_1$-$C_4$)-alkyl-;

R77 is selected from the series consisting of ($C_1$-$C_4$)-alkyl and R83-N(R84)-($C_1$-$C_4$)-alkyl-;

Het1 is a monocyclic, 4-membered to 7-membered, saturated, partially unsaturated or aromatic heterocycle which comprises 1, 2 or 3 identical or different ring heteroatoms selected from the series consisting of nitrogen oxygen and sulfur, and which is bonded via a ring carbon atom;

Het2 is a monocyclic, 4-membered to 7-membered, saturated heterocycle which comprises 1 or 2 identical or different ring heteroatoms selected from the series consisting of nitrogen, oxygen and sulfur;

Het3 is a monocyclic or bicyclic, 4-membered to 12-membered, saturated, partially unsaturated or aromatic heterocycle which comprises 1, 2 or 3 identical or different ring heteroatoms selected from the series consisting of nitrogen, oxygen and sulfur;

Het4 is a monocyclic, 4-membered to 7-membered, saturated heterocycle which comprises a ring nitrogen atom via which Het4 is bonded, and 0 or 1 further ring heteroatom selected from the series consisting of nitrogen, oxygen and sulfur;

wherein all phenyl groups are optionally substituted by one or more identical or different substituents selected from the series consisting of halogen, $(C_1-C_4)$-alkyl, cyano, hydroxy and $(C_1-C_4)$-alkyl-O—, unless specified otherwise;

wherein all cycloalkyl groups, independently of any other substituents which can be present on a cycloalkyl group, are optionally substituted by one or more identical or different substituents selected from the series consisting of fluorine and $(C_1-C_4)$-alkyl;

wherein all alkyl groups, independently of any other substituents which can be present on an alkyl group, are optionally substituted by one or more fluorine substituents.

12. A process for the preparation of a compound of the formula I as claimed in claim 1, which comprises reacting a compound of the formula II with a compound of the formula III to give a compound of the formula I in which X is =N— (formula Ia) and optionally, for the preparation of a compound of the formula I in which X is =N(O)— (formula Ib), oxidizing this compound, wherein the groups R1, R2, R3, R10 and R11 in the compounds of the formulae II and III are defined as in claim 1 for the compounds of the formula I

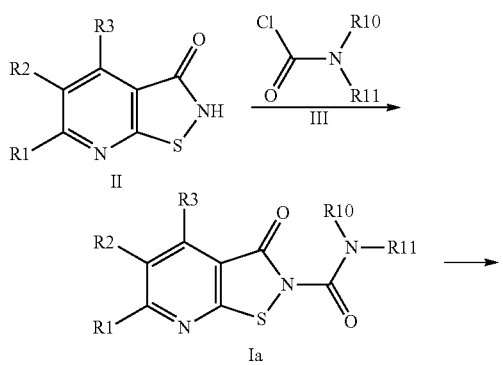

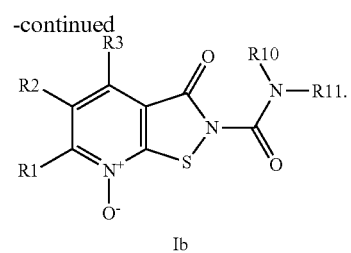

13. A pharmaceutical composition, comprising a compound of the formula I, in any of its stereoisomeric forms or a mixture of stereoisomeric forms in any ratio, or a pharmaceutically acceptable salt thereof, according to claim 1, and a pharmaceutically acceptable carrier.

14. A pharmaceutical composition, comprising a compound of the formula I, in any of its stereoisomeric forms or a mixture of stereoisomeric forms in any ratio, or a pharmaceutically acceptable salt thereof, according to claim 2, and a pharmaceutically acceptable carrier.

15. A pharmaceutical composition, comprising a compound of the formula I, in any of its stereoisomeric forms or a mixture of stereoisomeric forms in any ratio, or a pharmaceutically acceptable salt thereof, according to claim 7, and a pharmaceutically acceptable carrier.

16. A pharmaceutical composition, comprising a compound of the formula I, in any of its stereoisomeric forms or a mixture of stereoisomeric forms in any ratio, or a pharmaceutically acceptable salt thereof, according to claim 9, and a pharmaceutically acceptable carrier.

17. A pharmaceutical composition, comprising a compound of the formula I, in any of its stereoisomeric forms or a mixture of stereoisomeric forms in any ratio, or a pharmaceutically acceptable salt thereof, according to claim 10, and a pharmaceutically acceptable carrier.

18. A pharmaceutical composition, comprising a compound of the formula I, in any of its stereoisomeric forms or a mixture of stereoisomeric forms in any ratio, or a pharmaceutically acceptable salt thereof, according claim 11, and a pharmaceutically acceptable carrier.

19. A method of treating a disease selected from the group consisting of joint diseases, degenerative intervertebral disk diseases, osteoarthritis, neurodegenerative diseases, cancer, celiac disease, fibrosis and liver cirrhosis, comprising administering an efficacious amount of at least one compound of formula I, in any of its stereoisomeric forms or a mixture of stereoisomeric forms in any ratio, or a pharmaceutically acceptable salt thereof, according to claim 1 to a human or an animal in need thereof.

20. A method of inhibiting transglutaminases, comprising administering an efficacious amount of at least one compound of formula I, in any of its stereoisomeric forms or a mixture of stereoisomeric forms in any ratio, or a pharmaceutically acceptable salt thereof, according to claim 1 to a human or an animal in need thereof.

* * * * *

UNITED STATES PATENT AND TRADEMARK OFFICE
CERTIFICATE OF CORRECTION

| | | |
|---|---|---|
| PATENT NO. | : 9,260,454 B2 | Page 1 of 1 |
| APPLICATION NO. | : 14/307961 | |
| DATED | : February 16, 2016 | |
| INVENTOR(S) | : Hauke Szillat et al. | |

It is certified that error appears in the above-identified patent and that said Letters Patent is hereby corrected as shown below:

Claims

In column 70, line 39, in claim 18, delete "according" and insert -- according to --, therefor.

Signed and Sealed this
Twenty-fourth Day of May, 2016

Michelle K. Lee
*Director of the United States Patent and Trademark Office*